(12) United States Patent
Palushi et al.

(10) Patent No.: US 12,161,824 B2
(45) Date of Patent: Dec. 10, 2024

(54) MULTI-BALLOON DILATION CATHETER

(71) Applicant: Acclarent, Inc., Irvine, CA (US)

(72) Inventors: Jetmir Palushi, Irvine, CA (US); Fatemeh Akbarian, Rancho Palos Verdes, CA (US); David M. Locke, Springboro, OH (US); Athanasios Papadakis, Newport Beach, CA (US); Madison K. Vanosdoll, Irvine, CA (US)

(73) Assignee: Acclarent, Inc., Irvine, CA (US)

( * ) Notice: Subject to any disclaimer, the term of this patent is extended or adjusted under 35 U.S.C. 154(b) by 379 days.

(21) Appl. No.: 17/060,129

(22) Filed: Oct. 1, 2020

(65) Prior Publication Data

US 2021/0138207 A1    May 13, 2021

Related U.S. Application Data

(60) Provisional application No. 62/931,854, filed on Nov. 7, 2019.

(51) Int. Cl.
*A61M 25/10* (2013.01)
*A61B 17/12* (2006.01)
(Continued)

(52) U.S. Cl.
CPC ... *A61M 25/1011* (2013.01); *A61B 17/12104* (2013.01); *A61B 17/12136* (2013.01);
(Continued)

(58) Field of Classification Search
CPC ...... A61M 25/1011; A61M 2025/1013; A61M 2025/1061; A61M 2210/0618; A61B 17/12104; A61B 17/12136; A61B 17/24
See application file for complete search history.

(56) References Cited

U.S. PATENT DOCUMENTS

| 4,763,654 A | * | 8/1988 | Jang | A61M 25/1011 |
| | | | | 606/195 |
| 5,536,252 A | * | 7/1996 | Imran | A61M 25/1011 |
| | | | | 604/101.02 |

(Continued)

OTHER PUBLICATIONS

U.S. Appl. No. 62/931,854, filed Nov. 7, 2019, by Palushi et al., titled: "Multi-Balloon Dilation Catheter."

*Primary Examiner* — Kathleen S Holwerda
*Assistant Examiner* — Serenity A Miller
(74) *Attorney, Agent, or Firm* — Morgan, Lewis & Bockius LLP

(57) ABSTRACT

A method of dilating a target anatomical structure of an ear, a nose, or a throat of a patient includes inserting a distal end of a balloon catheter into the ear, the nose, or the throat. The balloon catheter includes a balloon assembly coaxially disposed along a proximally extending shaft. The balloon assembly includes at least first and second dilation balloons that at least partially overlap one another. The method also includes distally advancing the distal end until the balloon assembly is disposed in the target anatomical structure. The method also includes selectively dilating the target anatomical structure based on a diameter of the target anatomical structure by inflating the first dilation balloon to a first diameter or inflating the second dilation balloon to a second diameter that is greater than the first diameter. The second inflation lumen is not in fluid communication with the first inflation lumen.

20 Claims, 11 Drawing Sheets

(51) Int. Cl.
 *A61B 17/24* (2006.01)
 *A61M 29/02* (2006.01)

(52) U.S. Cl.
 CPC ....... *A61B 17/24* (2013.01); *A61M 25/10185* (2013.11); *A61M 29/02* (2013.01); *A61M 2025/1013* (2013.01); *A61M 2025/1061* (2013.01); *A61M 2210/0618* (2013.01); *A61M 2210/065* (2013.01); *A61M 2210/0662* (2013.01)

(56) References Cited

U.S. PATENT DOCUMENTS

| | | | |
|---|---|---|---|
| 6,083,205 A * | 7/2000 | Bourne | A61M 5/1408 604/99.01 |
| 6,156,053 A * | 12/2000 | Gandhi | A61M 25/1011 604/101.02 |
| 7,462,175 B2 | 12/2008 | Chang et al. | |
| 8,740,843 B2 | 6/2014 | Eaton et al. | |
| 8,827,953 B2 | 9/2014 | Rocha-Singh | |
| 9,186,485 B2 | 11/2015 | Gerrans et al. | |
| 10,070,993 B2 | 9/2018 | Chan et al. | |
| 10,327,897 B2 | 6/2019 | Madrid et al. | |
| 10,328,290 B2 | 6/2019 | Zhou et al. | |
| 10,350,396 B2 | 7/2019 | Chan et al. | |
| 10,512,763 B2 | 12/2019 | Jenkins et al. | |
| 10,813,589 B2 | 10/2020 | McKinney et al. | |
| 10,821,272 B2 | 11/2020 | Herrera et al. | |
| 2007/0073269 A1 * | 3/2007 | Becker | A61M 1/85 604/509 |
| 2007/0129751 A1 * | 6/2007 | Muni | A61M 25/0041 606/196 |
| 2008/0183128 A1 | 7/2008 | Morriss et al. | |
| 2010/0274188 A1 | 10/2010 | Chang et al. | |
| 2013/0138134 A1 | 5/2013 | Elman et al. | |
| 2013/0274715 A1 | 10/2013 | Chan et al. | |
| 2015/0290438 A1 | 10/2015 | Gerrans et al. | |
| 2018/0104404 A1 * | 4/2018 | Ngo-Chu | A61M 1/77 |
| 2020/0108238 A1 | 4/2020 | Matlock et al. | |

* cited by examiner

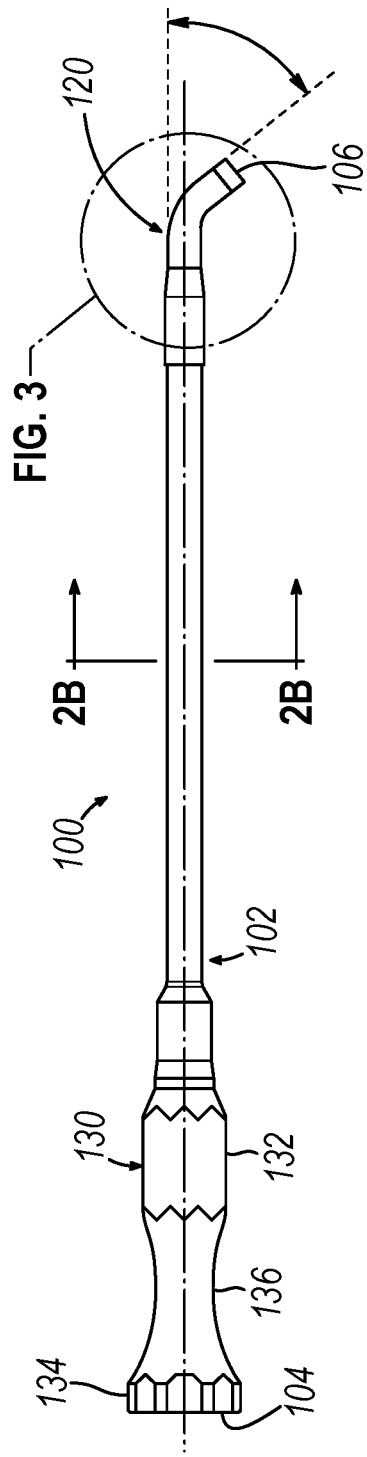
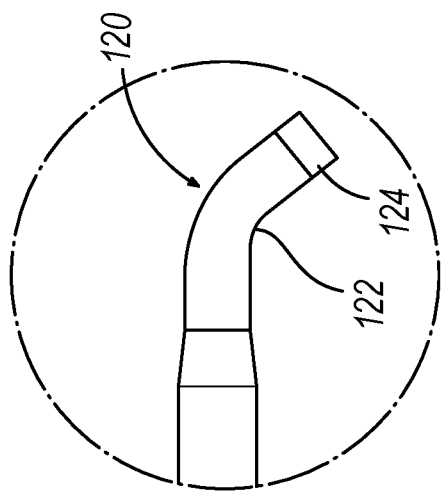
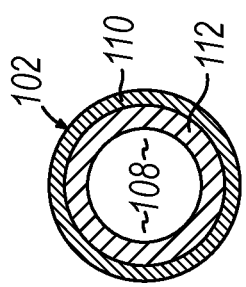
FIG. 2A
FIG. 2B
FIG. 3

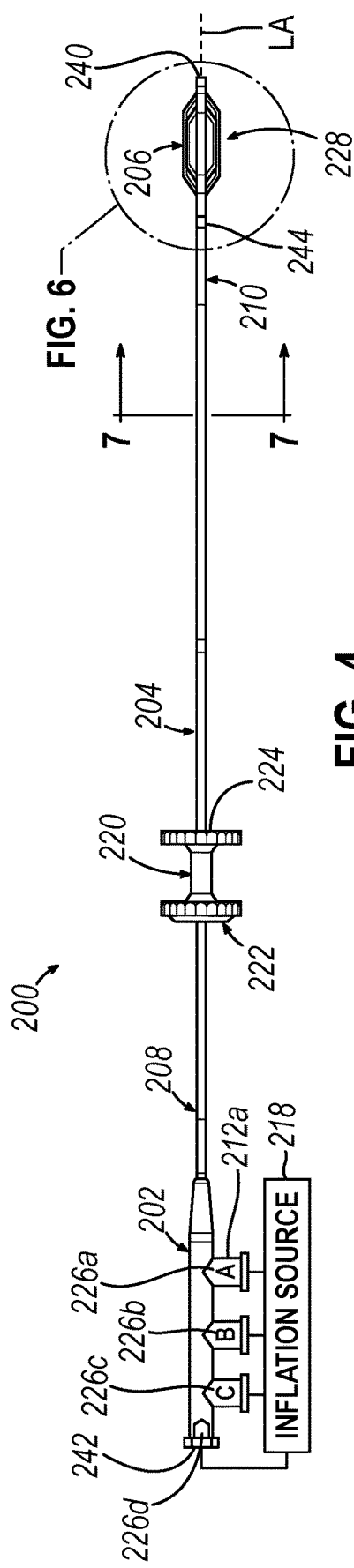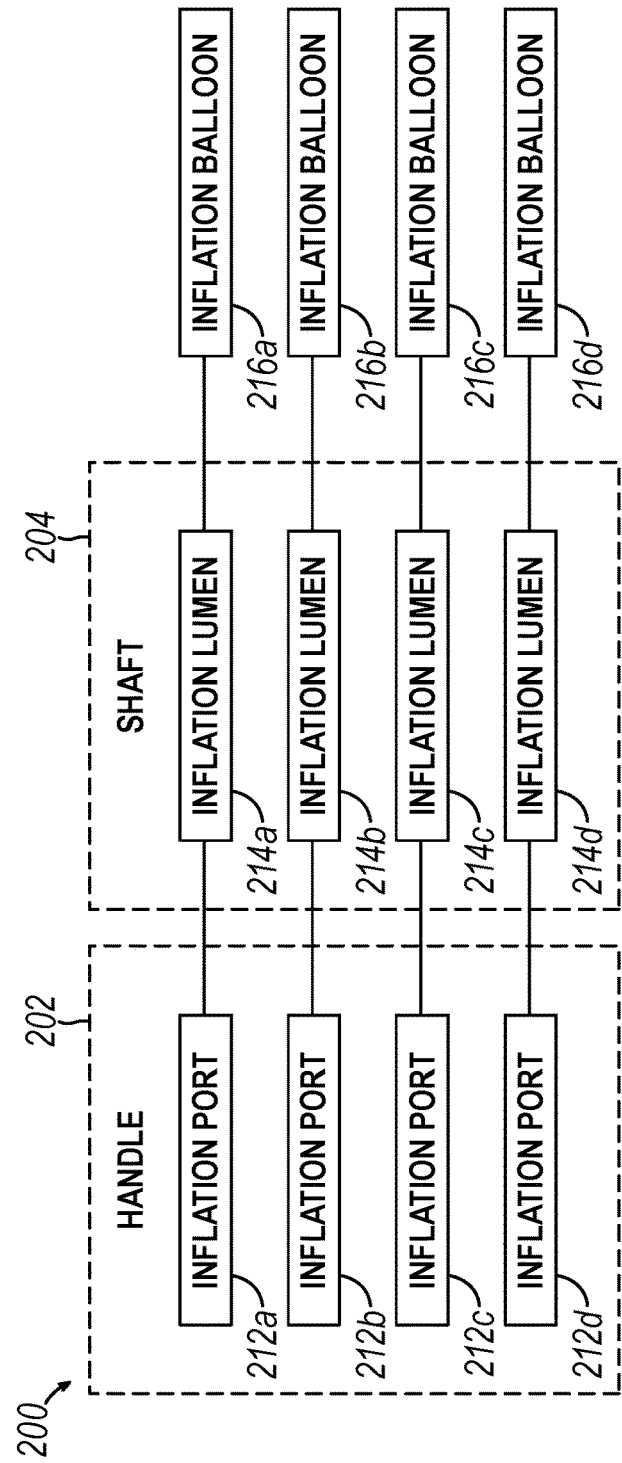

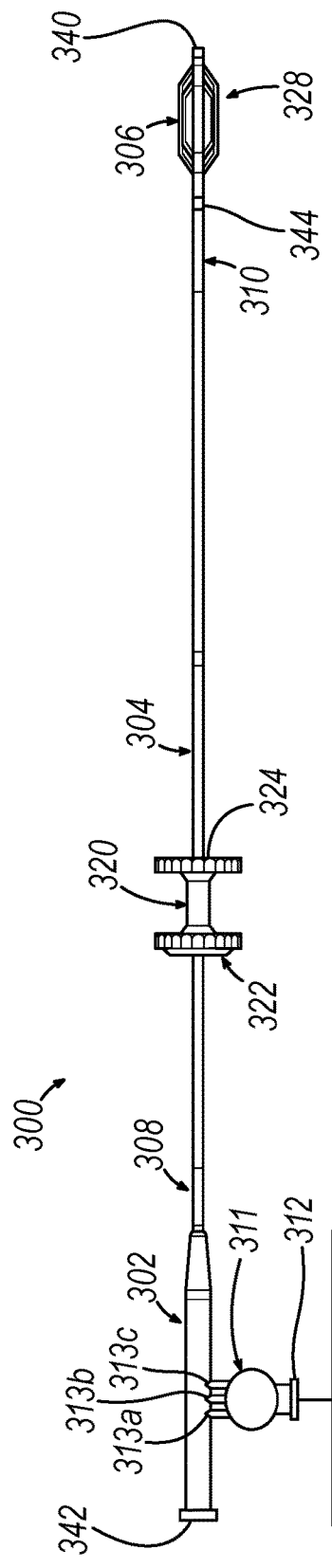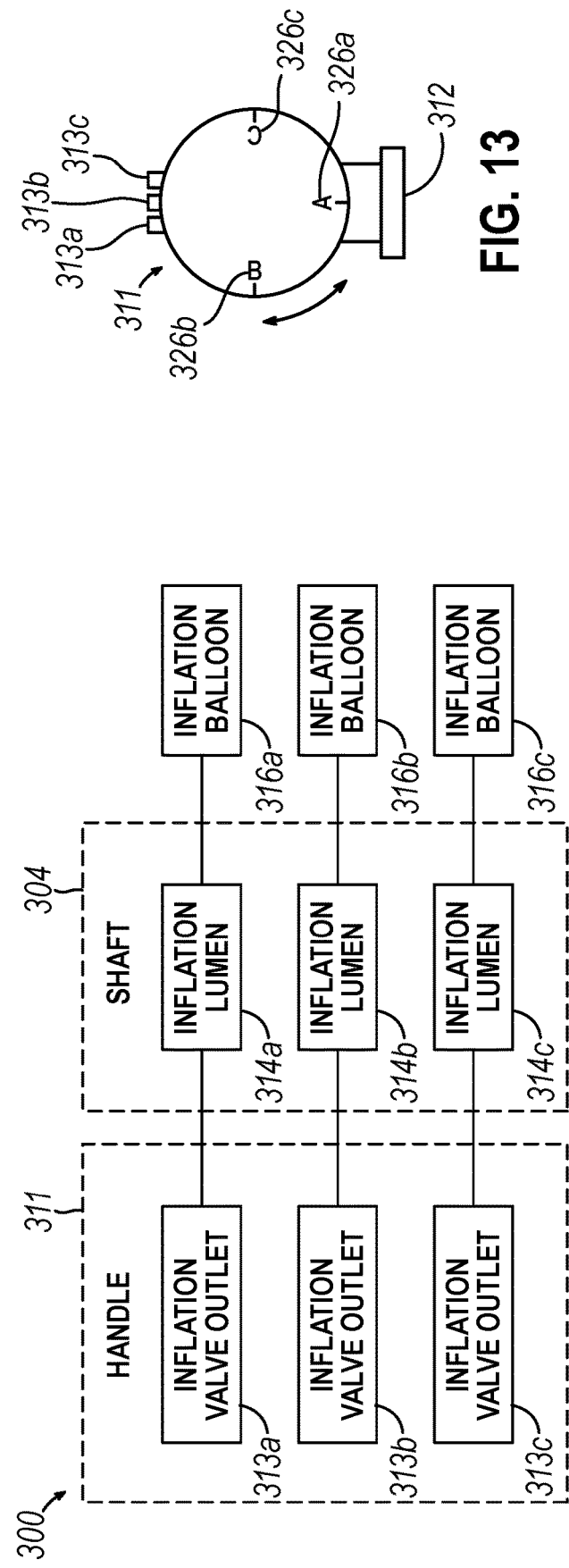

MULTI-BALLOON DILATION CATHETER

PRIORITY

This application claims priority to U.S. Provisional Pat. App. No. 62/931,854, entitled "Multi-Balloon Dilation Catheter," filed Nov. 7, 2019, the disclosure of which is incorporated by reference herein.

BACKGROUND

Referring to FIG. 1, the ear (10) is divided into three parts: an external ear (12), a middle ear (14), and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the sinuses. The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil), and stapes (38) (stirrup). These bones (34, 36, 38) transmit sound vibrations to the inner ear (16) and thereby act as a transformer, converting sound vibrations in the canal (20) of the external ear (12) into fluid waves in the inner ear (16).

The ET (26) is a narrow, one-and-a-half-inch long channel connecting the middle ear (14) with the nasopharynx (30), the upper throat area just above the palate, in back of the nose. The ET (26) functions as a pressure equalizing valve for the middle ear (14), which is normally filled with air. When functioning properly, the ET (26) opens for a fraction of a second periodically (about once every three minutes) in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the ET (26) may result in hearing impairment or other ear symptoms. A lining membrane (mucous membrane) of the middle ear (14) and ET (26) is connected with, and is the same as, the membrane of the nose (42), sinuses (44), and throat (32). Infection of these areas results in mucous membrane swelling which in turn may result in obstruction of the ET (26). This is referred to as serous otitis media, which as discussed above is essentially a collection of fluid in the middle ear (14).

Methods for treating the middle ear (14) and the ET (26) include those disclosed in U.S. Patent Pub. No. 2010/0274188, entitled "Method and System for Treating Target Tissue within the ET," published on Oct. 28, 2010, now abandoned, the disclosure of which is incorporated by reference herein; U.S. Patent Pub. No. 2013/0274715, entitled "Method and System for Eustachian Tube Dilation," published on Oct. 17, 2013, now abandoned, the disclosure of which is incorporated by reference herein; and U.S. Pat. No. 10,350,396, entitled "Vent Cap for a Eustachian Tube Dilation System," issued on Jul. 16, 2019, the disclosure of which is incorporated by reference herein. As described in those references, functioning of the ET (26) may be improved by dilating the ET (26) with an expandable dilator instrument.

While a variety of surgical instruments have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 2A depicts a side elevational view of an exemplary guide catheter;

FIG. 2B depicts a cross-sectional view of the guide catheter of FIG. 2A, taken along line 2B-2B in FIG. 2A;

FIG. 3 depicts an enlarged elevational view of the distal end of the guide catheter of FIG. 2A;

FIG. 4 depicts a side elevational view of an exemplary balloon dilation catheter that may be used with the guide catheter of FIG. 2A;

FIG. 5 depicts a schematic view of the balloon dilation catheter of FIG. 4;

FIG. 11 depicts a side elevational view of another exemplary balloon dilation catheter that may be used with the guide catheter of FIG. 2A;

FIG. 12 depicts a schematic view of the balloon dilation catheter of FIG. 11; and FIG. 13 depicts an enlarged elevational view of a valve of the hub of the balloon dilation catheter of FIG. 11.

Figure 1:
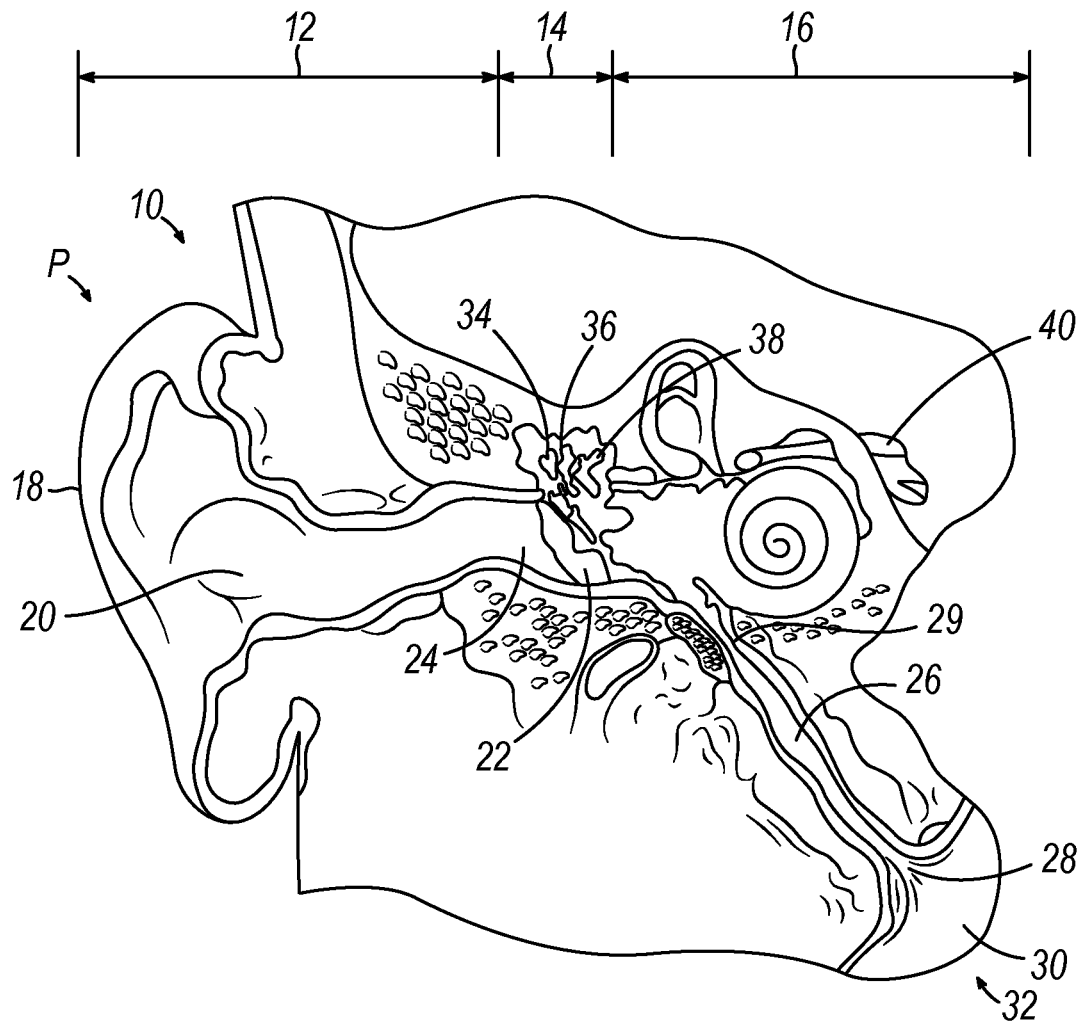
FIG. 1 depicts a cross-sectional view of a patient's head, showing the inner ear, the middle ear, the outer ear, and the Eustachian tube connecting the middle ear with the nasopharynx region of the throat.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Dilation Catheter System

Different target anatomical structures (S) of an ear (E), a nose (N), or a throat (T) of a patient (P) may require differently sized dilation balloons to sufficiently dilate the target anatomical structure (S). For this reason, it may be beneficial to include a product code or other identifying information on the balloon dilation catheter to indicate the particular size of the dilation balloon. For example, the product code may be attached to or imprinted onto the balloon dilation catheter. This allows the user to quickly and effectively determine the dilation diameter of the dilation balloon of the balloon dilation catheter. As such, when a user seeks to dilate a target anatomic structure to a certain diameter, the user refers to the specific indicia on the balloon dilation catheter.

While partially inflating a single dilation balloon and fully inflating the single dilation balloon may provide two effective dilation diameters, greater precision with respect to dilation diameters may be desired by users to prevent overdilating or underdilating the target anatomical structure (S). For example, overdilating the target anatomical structure (S) may result in temporary or permanent damage to the target anatomical structure (S), while underdilating the target anatomical structure (S) may not sufficiently open/clear the target anatomical structure (S), which may result in the procedure being generally ineffective or less effective than desired. This problem may be more pronounced with younger patients, especially children, as users (e.g. surgeons) may prefer to start with a smaller diameter balloon and, depending on the size of opening of the sinus drainage passageway or Eustachian Tube, decide whether to move to a larger diameter dilation balloon or not. For example, a larger diameter dilation balloon may be used to dilate the Eustachian tube of an adult patient, while a smaller diameter dilation balloon may be used to dilate the Eustachian tube of a child patient. Additionally, for example, a larger diameter dilation balloon may be used to dilate the Eustachian tube, while a smaller diameter dilation balloon may be used to dilate a sinus ostium or other passageway associated with drainage of a paranasal sinus.

To accommodate the above scenarios, some physicians may utilize two separate and distinct balloon dilation catheters. However, the desire to utilize two different balloon diameters generally necessitates using two different balloon catheters, where a first balloon dilation catheter with a dilation balloon having a first balloon diameter is inserted into the target anatomical structure (S). If the dilation balloon of that first dilation catheter does not effectively dilate the targeted anatomical cavity, then the first balloon dilation catheter is removed, and a second dilation catheter having a balloon with a larger diameter is inserted into the target anatomical cavity. Likewise, if the second balloon of the second dilation catheter does not effectively dilate the target anatomical cavity, then the second balloon dilation catheter is removed, and a third dilation catheter having a third balloon with a larger diameter is inserted into the target anatomical structure. This sequential removal and insertion may increase the duration of the procedure and/or may introduce an additional source of trauma for the patient (P).

It would be desirable to utilize a single balloon catheter that includes multiple dilation balloons of differing diameters to effectively dilate differently sized target anatomical structures (S) of the ear (E), the nose (N), or the throat (T) of the patient (P) without the problems described above. In other words, it may be desirable to provide a "universal" balloon catheter that is operable to dilate different anatomical passageways having different diameters within the same patient, and provide dilations in patients of various sizes (e.g., children and adults). An example of such a dilation system may include a guide (shown as a first exemplary guide catheter (100)) and a balloon dilation catheter (shown as first and second exemplary balloon dilation catheters (200, 300) as described below with reference to FIGS. 2A-13). The combination of guide catheter (100) and balloon dilation catheter (200, 300) may provide a compact system that is designed for a one-handed procedure. The compactness may help reduce interference with other instruments, such as an endoscope, which may be used to help in visualizing the positioning of the system, as described below. However, the use of the guide (e.g. guide catheter (100)) is merely optional and is not necessarily required with use of balloon dilation catheters (200, 300).

A. Exemplary Guide Catheter

FIGS. 2A-3 show guide catheter (100) as including an elongate shaft (102) with a proximal end (104), a distal end (106), and a lumen (108) extending therebetween. FIG. 2A shows a side elevational view of guide catheter (100). In some examples, guide catheter (100) may have a length between about 8 cm and about 20 cm in some versions, between about 10 cm and about 15 cm in some versions, or about 11 cm in some versions.

FIG. 2B shows a cross-sectional view of guide catheter (100) of FIG. 2A, taken along line 2B-2B in FIG. 2A. As shown, elongate shaft (102) includes an outer shaft tube (110) and an inner shaft tube (112) with lumen (108) disposed within inner shaft tube (112). FIG. 3 shows an enlarged elevational view of distal end (106) of guide catheter (100) of FIG. 2A. Distal portion (120) of guide catheter (100) may have a bend (122) at a predetermined angle to facilitate access into a particular passageway within the ear (E), the nose (N), or the throat (T) of a patient (P). In some versions, bend (122) is rigid. In such versions, the physician may have several different guide catheters (100) on hand, such that the physician may select a particular guide catheter (100) having a bend (122) with a bend angle that is particularly suited for accessing a targeted passageway. In some other versions, bend (122) is malleable, such that the physician may bend guide catheter (100) to achieve a bend angle that is particularly suited for accessing a targeted passageway. As yet another merely illustrative example, guide catheter (100) may include a steering feature (e.g., pull wire, etc.) that allows the physician to actively bend guide catheter (100) by manipulating an actuator.

As shown in FIG. 2A, proximal portion (130) of guide catheter (100) includes a proximal hub (132) that is ergonomically designed for insertion, location, and rotation through slight manipulations with one hand.

The foregoing features and configuration of guide catheter (100) are merely illustrative examples. Guide catheter (100) may instead have any other suitable features and configuration as will be apparent to those skilled in the art in view of the teachings herein.

B. First Exemplary Balloon Dilation Catheter

FIGS. 4-7 show a first exemplary balloon dilation catheter (200) that may be used with guide catheter (100) of FIG. 2A. Balloon dilation catheter (200) of the present example includes a hub (202), an elongate shaft (204), and a balloon assembly (206). Elongate shaft (204) includes a proximal portion (208) and a distal portion (210) disposed opposite proximal portion (208). Hub (202) is coupled with proximal portion (208) of elongate shaft (204). Balloon assembly (206) may be coupled with distal portion (210) of elongate shaft (204) and is coaxially disposed along elongate shaft (204). As shown, elongate shaft (204) extends proximally from balloon assembly (206). Balloon assembly (206) includes at least two dilation balloons that at least partially overlap one another to form an overlapping series of dilation balloons.

As will be described in greater detail below, a user couples an inflation source (218) with one of inflation ports (212a-d) that is fluidly coupled with a respective inflation lumen of inflation lumens (214a-d) which is fluidly coupled with a respective dilation balloon of dilation balloons (216a-d). This allows the user to achieve a predetermined dilation diameter (d1-d4) for a desired procedure by selecting the desired port (e.g. inflation ports (212a-d)) that corresponds to a particular dilation balloon (216a-d). This may prevent a user (e.g. a surgeon) from having to sequentially insert multiple balloon dilation catheters having different sized dilation balloons to treat the target anatomical structure (S).

As shown in FIG. 4, balloon dilation catheter (200) includes an actuator (220). Actuator (220) includes a proximal side (222) and a distal side (224). In the example shown in FIG. 4, actuator (220) may be secured by an adhesive to elongate shaft (204). Actuator (220) allows for easy, ergonomic one-handed advancement of balloon dilation catheter (200) through guide catheter (100) and into the target anatomical structure (S) (e.g. the ET (26)). Actuator (220) may be used to advance or retract in alternative ways including but not limited to use of the thumb, the index finger, or a combination of fingers (e.g., the index and middle fingers) or the thumb and the index or middle finger.

With continued reference to FIG. 4, hub (202) includes indicia (226a-d) near ports (212a-d) indicating information regarding characteristics of dilation balloons (216a-d). This ensures that the desired inflation diameter (d1-d4) of balloon assembly (206) particularly matches indicia (226a-d) located on respective ports (212a-d) of hub (202). For example, indicia (226a-d) may include dilation diameters (d1-d4), or a desired location for the specific diameter of the respective balloon, etc.

A method of dilating the target anatomical structure (S) of the ear (E), the nose (N), or the throat (T) of the patient (P) is described below with respect to the following figures. By way of example only, the target anatomical structure (S) may correspond to a Eustachian tube, a larynx, a choana, a sphenoid sinus ostium, one or more openings associated with one or more ethmoid sinus air cells, a maxillary sinus ostium, the frontal recess, and/or other passageways associated with paranasal sinuses. For example, the target anatomical structure (S) may be selected from a group consisting of a middle ear cavity, a sinus cavity, a nasal airway, or ET (26) of the ear (E), the nose (N), or the throat (T) of the patient (P). Additionally, while the shown target anatomical structure (S) is hourglass shaped, it is envisioned that the target anatomical structure (S) may have a variety of shapes and sizes. As such, the target anatomical structure (S) may vary from the shown target anatomical structure (S).

Figure 6:
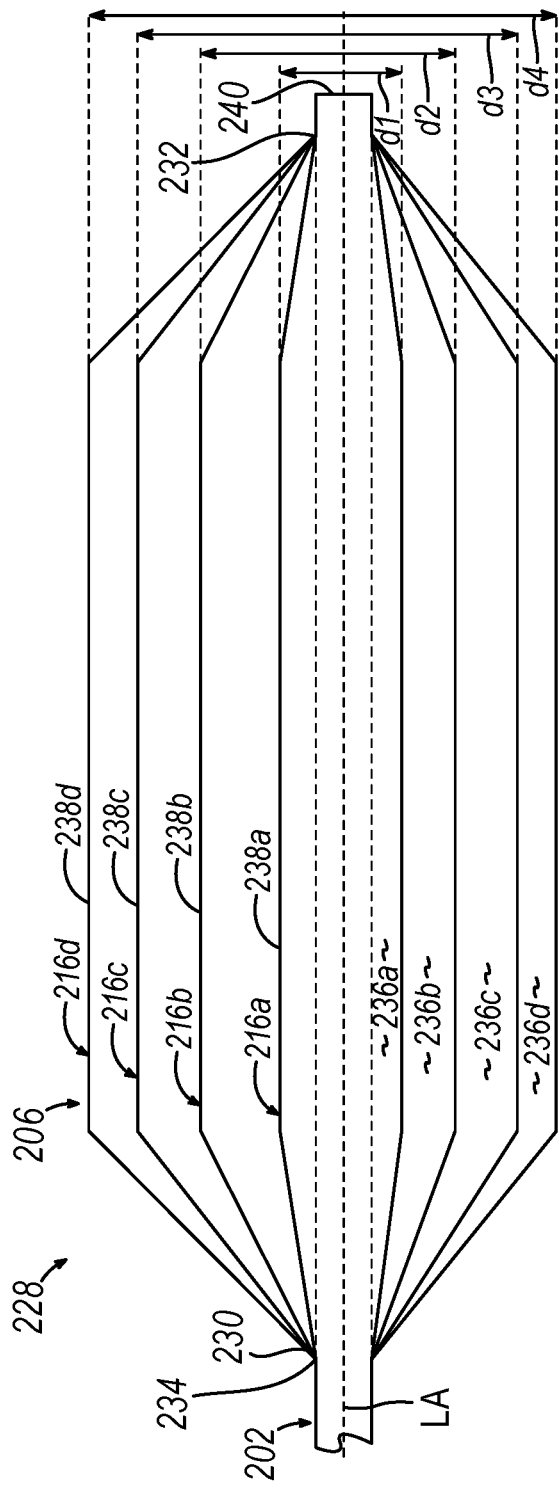
FIG. 6 depicts an enlarged elevational view of the distal end of the balloon dilation catheter of FIG. 4.

As shown in FIGS. 4-6, different inflation ports (212a-d) may be used to achieve different dilation diameters (d1-d4) in an expanded/inflated configuration. FIG. 5 shows a schematic view of balloon dilation catheter (200) of FIG. 4. As shown, hub (202) includes inflation ports (212a-d), elongate shaft (204) includes inflation lumens (214a-d), and balloon assembly (206) includes dilation balloons (216a-d). In other words, balloon dilation catheter (200) includes four inflation ports, four inflation lumens, and four dilation balloons. However, greater or fewer inflation ports, inflation lumens, and dilation balloons are also envisioned. For example, balloon dilation catheter (200) may include two inflation ports, two inflation lumens, and two dilation balloons. Alternatively, for example, balloon dilation catheter (200) may include three inflation ports, three inflation lumens, and three dilation balloons.

As shown, each dilation balloon (216a-d) may be fed by a dedicated inflation lumen (214a-d) on a 1:1 basis. For example, dilation balloon (216a) may be inflated to diameter (d1) by fluidly coupling inflation source (218) (see FIG. 4) with port (212a) that is in fluid communication with dilation balloon (216a) using inflation lumen (214a) that extends through elongate shaft (204) to dilate target anatomical structure (S) to diameter (d1). Dilation balloon (216b) may be inflated to diameter (d2), which is greater than diameter (d1) but less than diameters (d3, d4), by fluidly coupling inflation source (218) with port (212b) that is in fluid communication with dilation balloon (216b) using inflation lumen (214b). Inflation lumen (214b) extends through elongate shaft (204) to selectively inflate dilation balloon (216b) to dilate target anatomical structure (S) to diameter (d2). Inflation lumen (214b) is not in fluid communication with (i.e. fluidically isolated from) inflation lumens (214a, 214c-d).

Similarly, dilation balloon (216c) may be inflated to diameter (d3), which is greater than diameters (d1, d2) but is less than diameter (d4), by inserting inflation fluid from inflation source (218) through inflation lumen (214c) to selectively dilate target anatomical structure (S). Inflation lumen (214c) is not in fluid communication with either of inflation lumens (214a-b, 214d). Similarly, dilation balloon (216d) may be inflated to diameter (d4) by inserting inflation fluid from inflation source (218) through inflation lumen (214d). Inflation lumen (214d) is not in fluid communication with any of inflation lumens (214a-c). Diameter (d4) is greater than any of diameters (d1-d3). Dilation balloons (216a-d) may be inflated to a predetermined pressure. While not shown, if additional length is desired, multiple balloons may be used in series (e.g. distal and proximal balloons (not shown)) and may be placed and inflated with different lumens. Balloon dilation catheter (200) allows a larger diameter dilation balloon to be used to dilate target anatomical structure (S) (e.g. the Eustachian tube) of an adult patient, while a smaller diameter dilation balloon may be used to dilate the target anatomical structure (S) of a child patient.

FIG. 6 shows an enlarged elevational view of distal portion (228) of balloon dilation catheter (200) of FIG. 4. As shown, dilation balloons (216a-d) are approximately coextensive with one another along longitudinal axis (LA). As such, each of dilation balloons (216a-d) may terminate generally the same proximal end (230) and generally the same distal end (232), except for a small region to accommodate inflation lumens (214a-c) to provide inflation fluid to respective dilation balloons (216a-c). For example, the small region is shown as a proximally located connection (234) for inflating/activating dilation balloons (216a-d) by communicating a pressurized inflation fluid (e.g., saline) to inflation lumens (214a-d) of respective dilation balloons (216a-d) of balloon assembly (206). As shown, each of dilation balloons (216a-d) includes an interior cavity (236a-d) defined by a balloon wall (238a-d). As shown, balloon assembly (206) is disposed proximal to a distal tip (240) of elongate shaft (204); however, this arrangement may vary in some versions.

Balloon dilation catheter (200) may include a range of suitable sized dilation balloons (216a-d) including, but not limited to, balloons of 2 mm to 8 mm in diameter or of between about 5 mm and 6 mm (when inflated) and 12 mm to 24 mm in working length (e.g., 2 mm×12 mm, 3.5 mm×12 mm, 5 mm×16 mm, 5 mm×24 mm, 6 mm×16 mm, 6 mm×20 mm, 6 mm×24 mm, 7 mm×16 mm, or 7 mm×24 mm). In at least some applications, a maximum outer diameter of approximately 6 mm provides sufficient dilation of patient's target anatomical structure (S) (e.g. ET (26) for an ET dilation procedure). It will be appreciated, however, that dilation balloons (216a-d) may be suitably configured to assume other maximum sizes for use in other applications and dilation procedures. Each dilation balloon (216a-d) of the present example may have a working length of approximately 12 mm to approximately 24 mm. In other examples, each balloon (216a-d) may have a working length of approximately 20 mm to approximately 40 mm. According to one exemplary embodiment, diameter (d1) may be approximately 3 mm, diameter (d2) may be approximately 5 mm, and diameter (d3) may be approximately 6 mm. Alternatively, according to another exemplary embodiment, diameter (d1) may be approximately 6 mm, diameter (d2) may be approximately 7 mm, and diameter (d3) may be approximately 8 mm.

Figure 7:
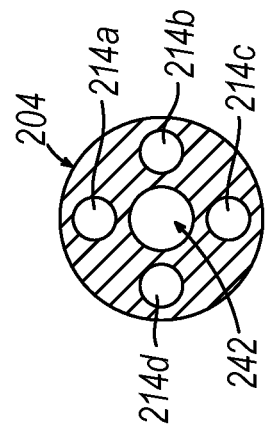
FIG. 7 depicts a cross-sectional view of a shaft of the balloon dilation catheter of FIG. 4, taken along line 7-7 of FIG. 4.
Figure 8A:
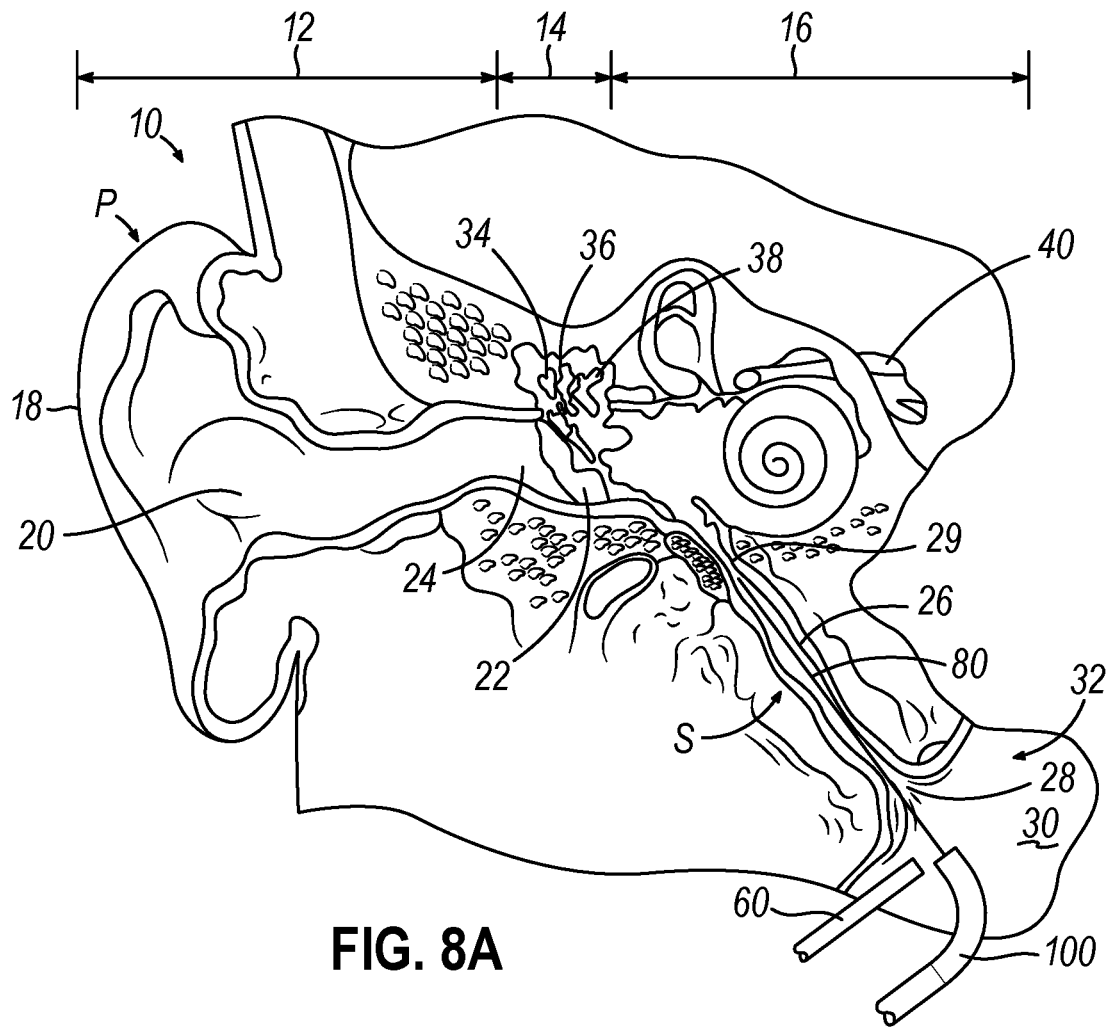
FIG. 8A depicts a cross-sectional view of a patient's head, with the guide catheter of FIG. 2A, a guidewire, and an endoscope being positioned in relation to the patient's Eustachian tube via the throat.
Figure 9A:
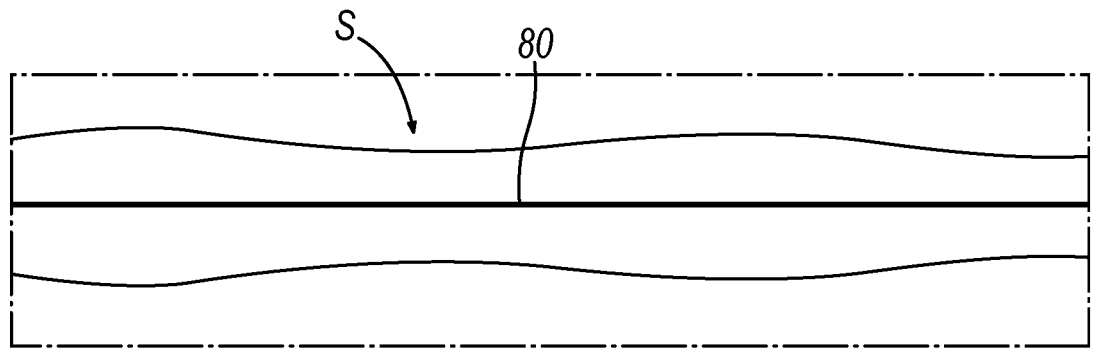
FIG. 9A depicts a cross-sectional view of a portion of the guidewire and Eustachian tube of FIG. 8A, with the guidewire positioned within the Eustachian tube.

FIG. 7 shows a cross-sectional view of elongate shaft (204) of balloon dilation catheter (200) of FIG. 6, taken along line 7-7 in FIG. 4. As shown in FIG. 7, elongate shaft (204) includes inflation lumens (214a-c) to dilate dilation balloons (216a-d) respectively. Elongate shaft (204) may include a guidewire lumen (242), shown as being centrally disposed, configured to receive a guidewire (80) therethrough as shown in FIGS. 8A and 9A.

In some versions, distal tip (240) includes an enlarged, bulbous feature. Such a bulbous feature may be sized and configured to prevent distal tip (240) from passing through an isthmus (29) of an ET (26). In some versions, dilation catheter (200) is configured such that the bulbous tip may be selectively inflated to transition between an expanded state (e.g., for when dilation catheter (200) is being used to dilate an ET) and a non-expanded state (e.g., for when dilation catheter (200) is being used to dilate some other passageway). Such an inflatable bulbous tip may be configured and operable in accordance with at least some of the teachings of U.S. Pat. No. 10,512,763, entitled "Dilation Catheter with Expandable Stop Element," issued Dec. 24, 2019, the disclosure of which is incorporated by reference herein in its entirety. In some other versions, dilation catheter (200) is configured such that the bulbous tip may be selectively removed, such as by cutting the bulbous tip, unscrewing the bulbous tip, or otherwise removing the bulbous tip. Such versions may be configured and operable in accordance with at least some of the teachings of U.S. Pub. No. 2020/0108238, entitled "Dilation Catheter Tip Removal Instrument," published Apr. 9, 2020, the disclosure of which is incorporated by reference herein in its entirety. Alternatively, dilation catheter (200) may include a bulbous tip in any other suitable fashion; or may lack a bulbous tip.

C. Exemplary Method of Dilating the ET Through the Throat

FIGS. 8A-9C show an exemplary method for using balloon dilation catheter (200) described above to dilate the target anatomical structure (S) shown as the ET (26) through the throat (T) of the patient (P). While the present example is being provided in the context of dilating the ET (26), it should be understood that balloon dilation catheter (200) may be used for various other procedures. By way of example only, balloon dilation catheter (200) and variations thereof may be used to dilate a larynx, a choana, a sphenoid sinus ostium, one or more openings associated with one or more ethmoid sinus air cells, a maxillary sinus ostium, the frontal recess, and/or other passageways associated with paranasal sinuses. Other suitable ways in which balloon dilation catheter (200) may be used will be apparent to those skilled in the art in view of the teachings herein.

The method may optionally include inserting distal end (106) of guide catheter (100) into the patient (P). FIG. 8A shows a cross-sectional view of a patient's head, with the guide catheter (100) of FIG. 2A, a guidewire (80), and an endoscope (60) being positioned in relation to the patient's ET (26) via the throat (T). FIG. 9A shows a cross-sectional view of a portion of FIG. 8A, with guidewire (80) positioned within the ET (26). Distal end (106) of guide catheter (100) may be distally advanced until distal end (106) is near target anatomical structure (S). Guide catheter (100) may be stopped short of the target anatomical structure (S) to allow for one or more dilation balloons (216a-d) of balloon assembly (206) to expand within target anatomical structure (S).

Once guide catheter (100) is positioned in the patient (P), a distal end of balloon dilation catheter (200) may be advanced via guide catheter (100) into the ear (E), the nose (N), or the throat (T) of the patient (P). Balloon assembly (206) may be expanded to dilate the target anatomic structure (S) after balloon assembly (206) is placed in the target anatomic structure (S). For example, the opening area of the ET (26) includes a pharyngeal ostium (28), and balloon dilation catheter (200) may be advanced to pass balloon assembly (206) through the pharyngeal ostium (28) and into the ET (26), as shown in FIGS. 8B and 9B.

Distal portion (228) of balloon dilation catheter (200) may be distally advanced until balloon assembly (206) is disposed in target anatomical structure (S) of the ear (E), the nose (N), or the throat (T) of the patient (P). An endoscope (60) may be used to assist in positioning balloon dilation catheter (200). Endoscope (60) may be advanced through the nasal passage to view balloon dilation catheter (200). A marker (244) (see FIG. 4) on elongate shaft (204) of balloon dilation catheter (200) may be viewed from endoscope (60) to approximate a location of balloon assembly (206) relative to the opening of the ET (26) (e.g., pharyngeal ostium (28)) based on a distance of the marker (244) from a proximal end of balloon assembly (206). Accordingly, balloon dilation catheter (200) may be moved to place marker (244) in a desirable location before expansion of the balloon assembly (206) in the ET (26).

The target anatomical structure (S) of the ear (E), the nose (N), or the throat (T) of the patient (P) may be selectively dilated based on a desired dilation diameter (d1-d4) of target anatomical structure (S). Sequential dilation of dilation balloons (216a-d) is also envisioned as shown when comparing FIGS. 8B and 9B with FIGS. 8C and 9C. As described above, one dilation balloon (216a-c) may be inflated prior to another of dilation balloons (216b-d) being inflated. In some instances, it may be beneficial to dilate the target anatomical structure (S) in a sequence, from a smaller diameter to a larger diameter (e.g. diameter (d1) to diameter (d2) to diameter (d3) to diameter (d4)). It is envisioned that dilation balloon (216b) may be inflated prior to dilation balloons (216c-216d) being inflated, with or without dilation balloon (216a) being inflated. Similarly, dilation balloon (216c) may be inflated prior to dilation balloon (216d) being inflated, with or without dilation balloons (216a-b) being inflated. As previously described, balloon dilation catheter (200) allows a larger diameter dilation balloon to be used to dilate target anatomical structure (S) (e.g. the Eustachian tube) of an adult patient, while a smaller diameter dilation balloon may be used to dilate the target anatomical structure (S) of a child patient. The size of the patient (P) accounts for the age of the patient (P).

Figure 8B:
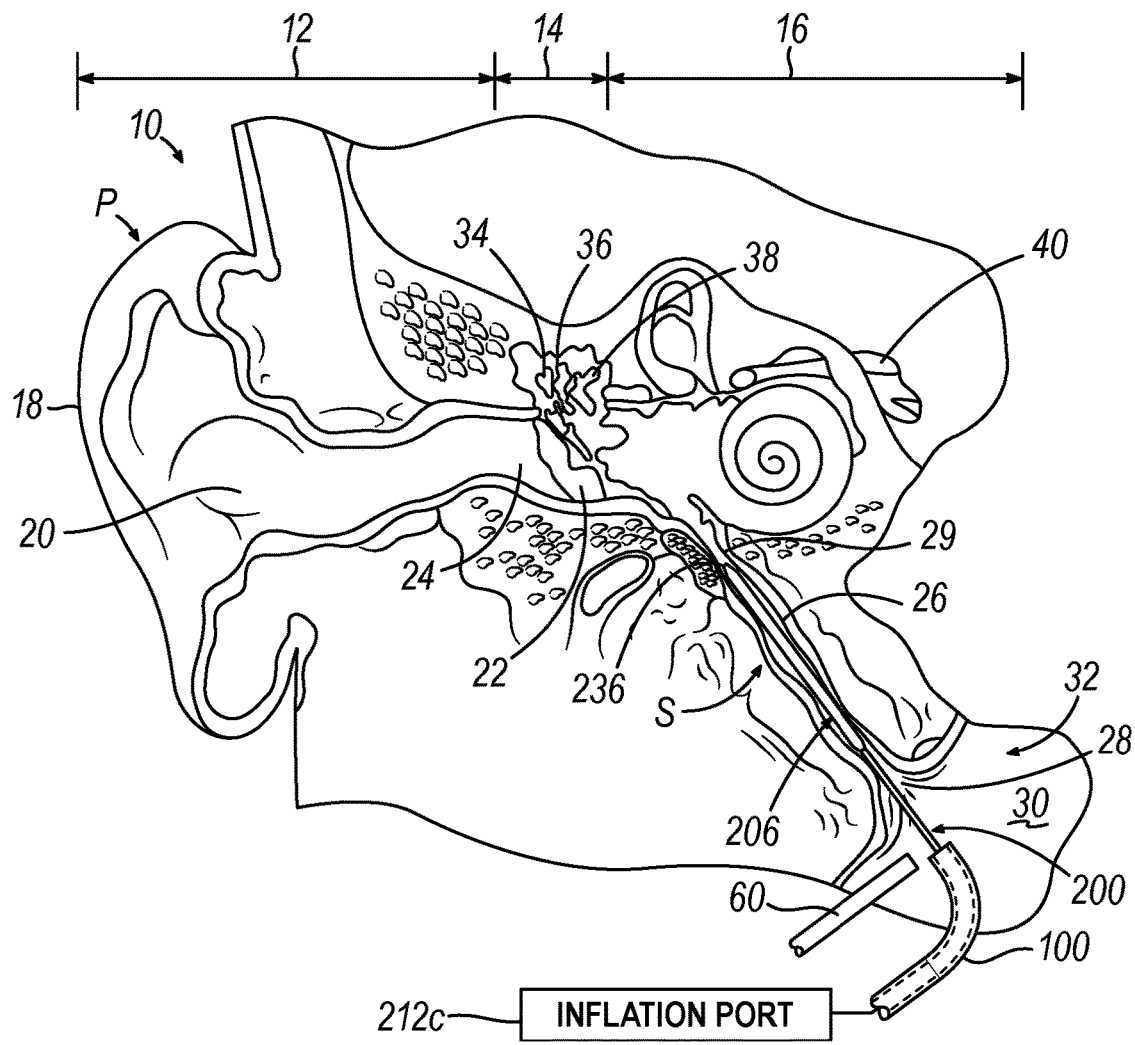
FIG. 8B depicts a cross-sectional view of the patient's head of FIG. 8A, with the balloon dilation catheter of FIG. 4 inserted into the Eustachian tube and subsequently expanded to dilate the Eustachian tube to a first diameter.
Figure 9B:
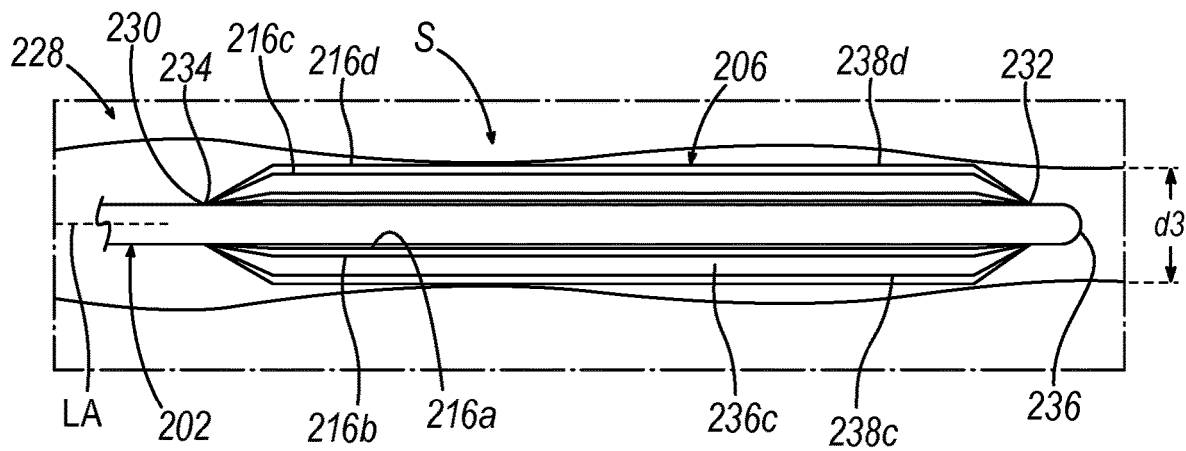
FIG. 9B depicts a cross-sectional view of a portion of the balloon dilation catheter and Eustachian tube of FIG. 8B, with the balloon dilation catheter inserted into the Eustachian tube and subsequently expanded to dilate the Eustachian tube to a first diameter.

FIG. 8B shows a cross-sectional view of the patient's head of FIG. 8A, with balloon dilation catheter (200) of FIG. 4 inserted into the ET (26) and subsequently expanded to dilate ET (26) to diameter (d3). FIG. 9B shows a cross-sectional view of a portion of FIG. 8B, with balloon dilation catheter (200) inserted into ET (26) and subsequently expanded to dilate ET (26) to diameter (d1). After balloon assembly (206) is positioned within the ET (26) and inflated to an expanded state, balloon assembly (206) may be held in location while in an expanded state for an extended period of time (e.g. several seconds or minutes). As shown in FIGS. 8B and 9B, dilation balloon (216c) may be inflated to diameter (d3), which is greater than diameters (d1, d2) but is less than diameter (d4), by inserting inflation fluid from inflation source (218) through inflation lumen (214c) to selectively dilate target anatomical structure (S). Inflation lumen (214c) is not in fluid communication with either of inflation lumens (214a-b, 214d). Dilation balloon (216c) may be inflated to a predetermined pressure.

Figure 8C:
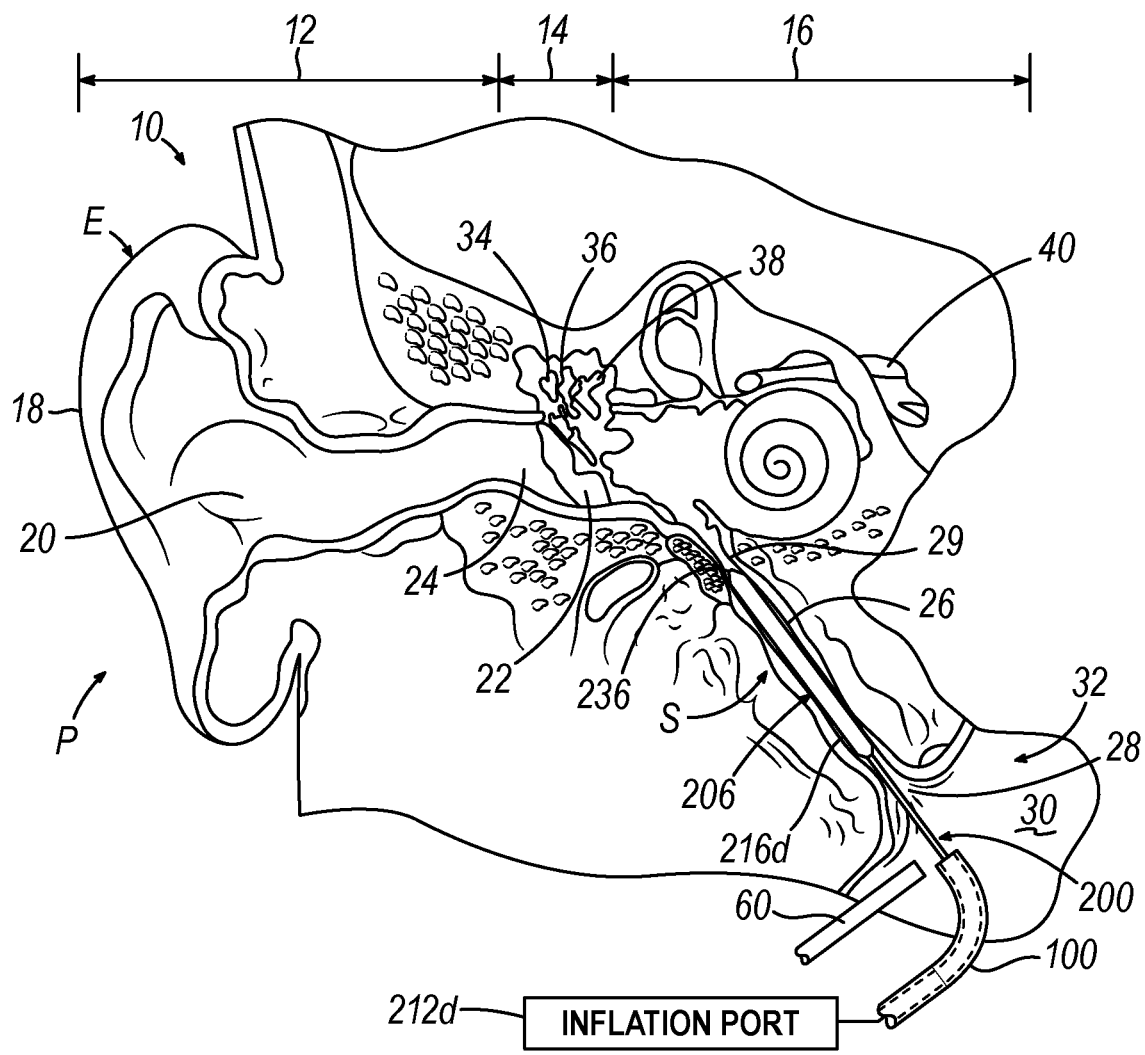
FIG. 8C depicts a cross-sectional view of the patient's head of FIG. 8B, with the balloon dilation catheter expanded to dilate the Eustachian tube to a second diameter.
Figure 9C:
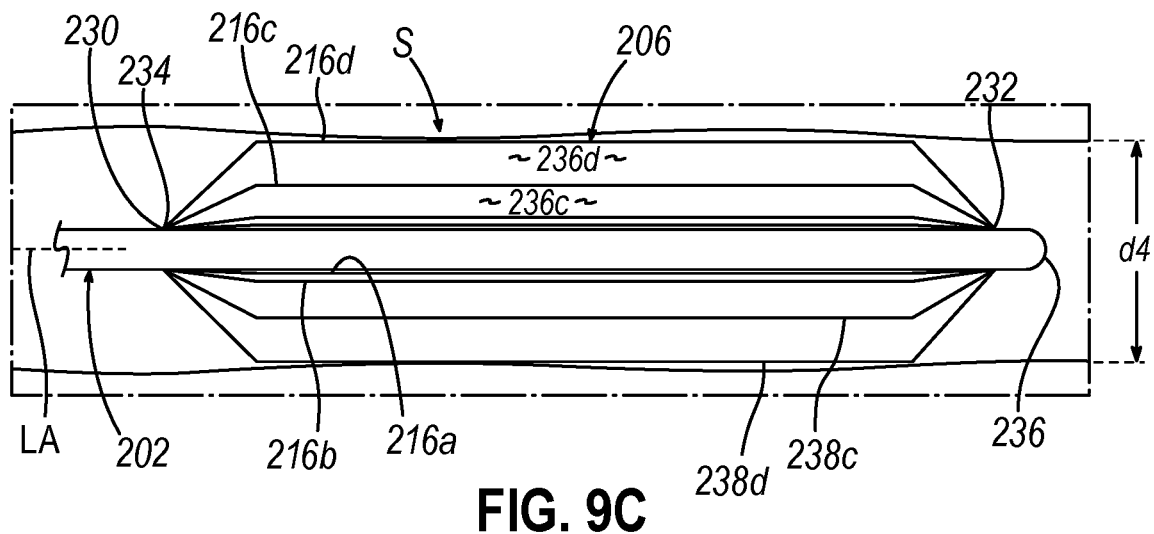
FIG. 9C depicts a cross-sectional view of a portion of the balloon dilation catheter and Eustachian tube of FIG. 8C, with the balloon dilation catheter expanded to dilate the Eustachian tube to a second diameter.

FIG. 8C shows a cross-sectional view of the patient's head of FIG. 8B, with balloon dilation catheter (200) expanded to dilate ET (26). FIG. 9C shows a cross-sectional view of a portion of FIG. 8C, with balloon dilation catheter (200) expanded to dilate ET (26) to diameter (d4). As shown in FIGS. 8C and 9C, dilation balloon (216d) may be inflated to diameter (d4) by inserting inflation fluid from inflation source (218) through inflation lumen (214d). Diameter (d4) is greater than any of diameters (d1-d3). Inflation lumen (214d) is not in fluid communication with any of inflation lumens (214a-c). As shown, exterior surface (238d) of dilation balloon (216d) is in contact with inner wall of target anatomical structure (S). Dilation balloon (216d) may be inflated to a predetermined pressure.

After balloon assembly (206) has been deflated/unexpanded, balloon dilation catheter (200) and guide catheter (100) may be removed from the patient. The ET (26) will resume functioning, normally opening and closing to equalize atmospheric pressure in the middle ear (14) and protect the middle ear (14) from unwanted pressure fluctuations and loud sounds.

D. Exemplary Method for Dilating the Ostium of a Maxillary Sinus

Figure 10A:
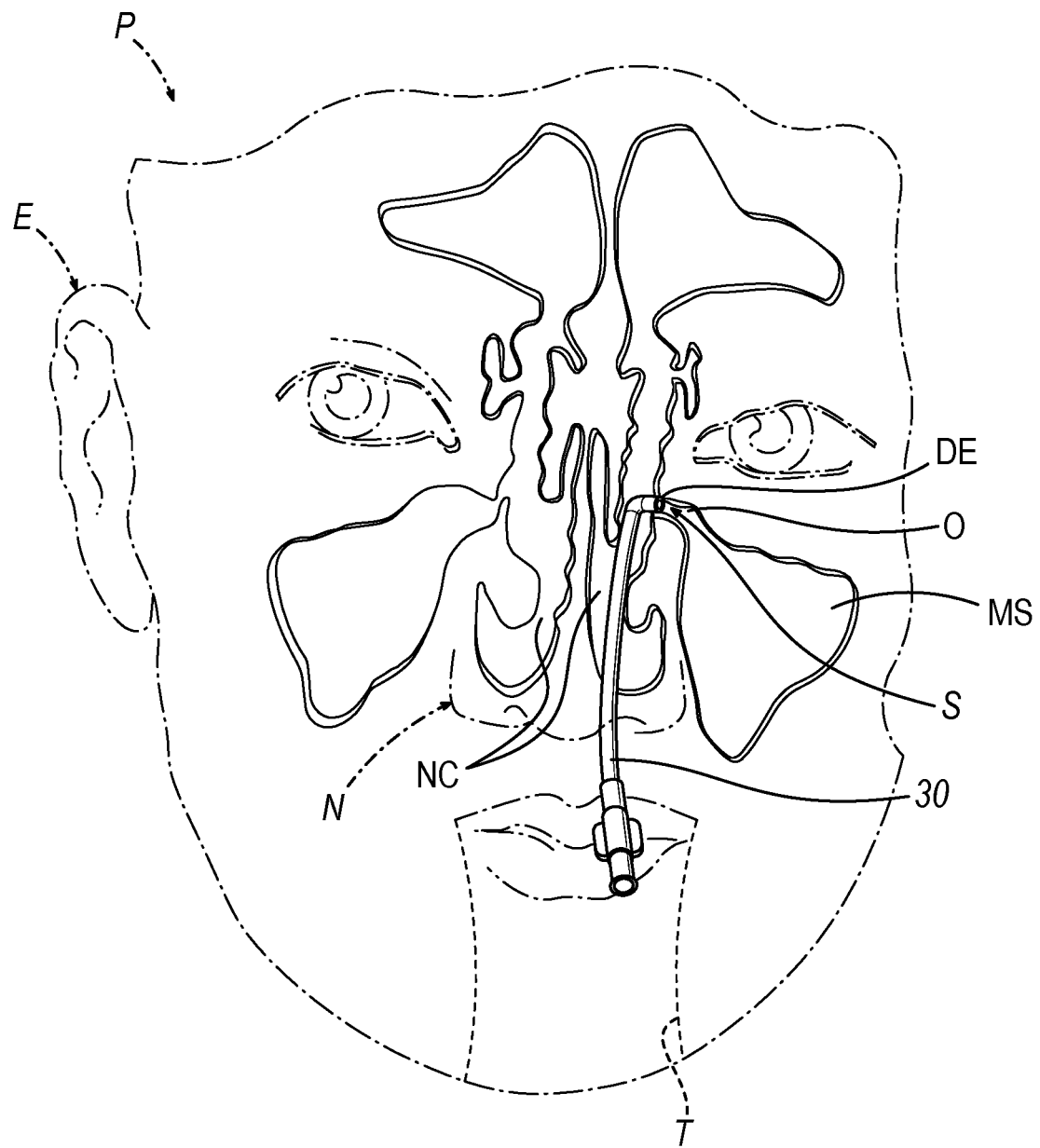
FIG. 10A depicts a front view of the guide catheter of FIG. 2A positioned adjacent an ostium of the maxillary sinus.
Figure 10B:
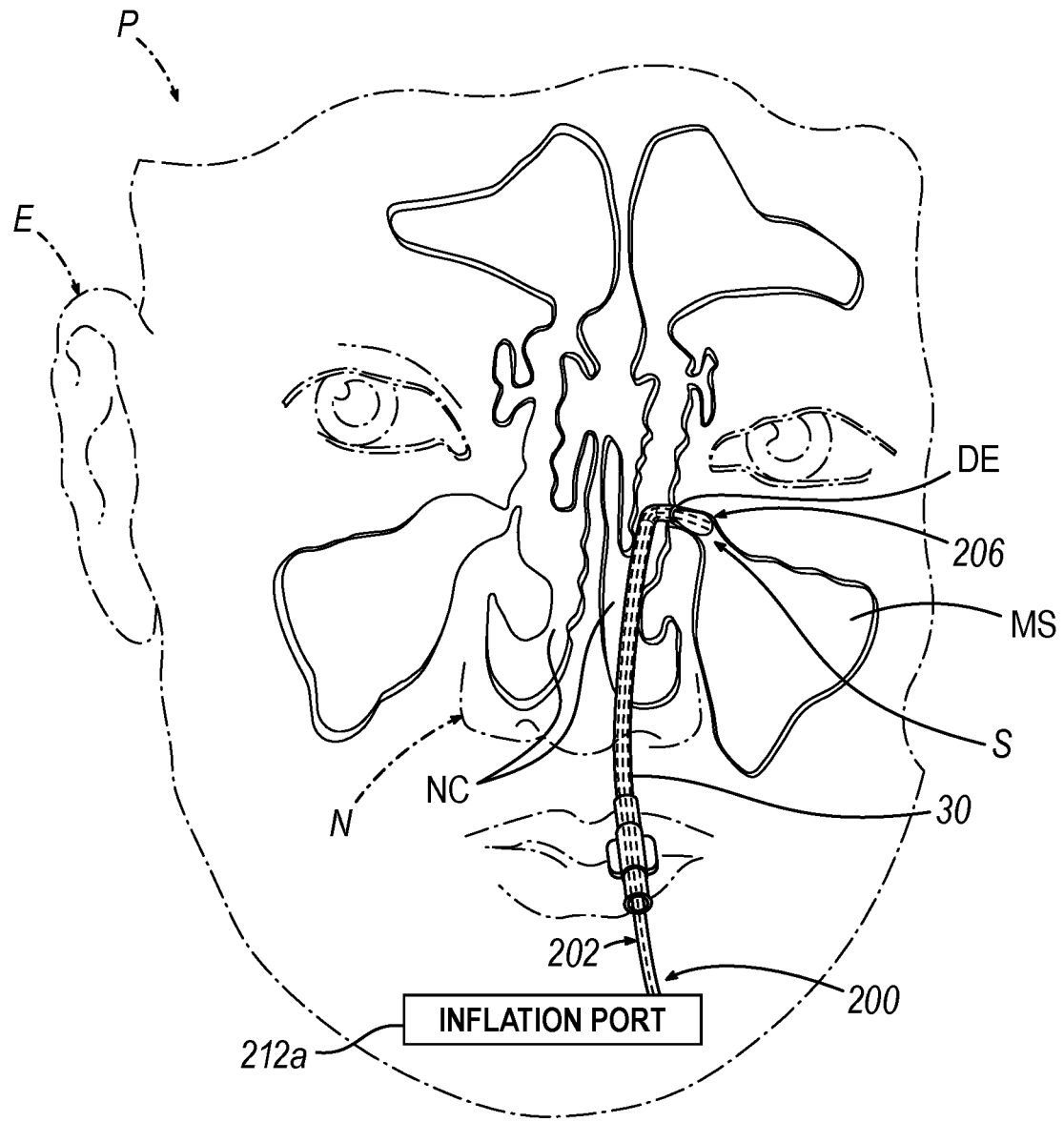
FIG. 10B depicts a front view of the guide catheter of FIG. 2A positioned adjacent an ostium of the maxillary sinus, with the dilation catheter of FIG. 4 translated distally relative to the guide catheter along the guidewire of FIG. 2A so as to position a dilation balloon of the balloon dilation catheter within the ostium.
Figure 10C:
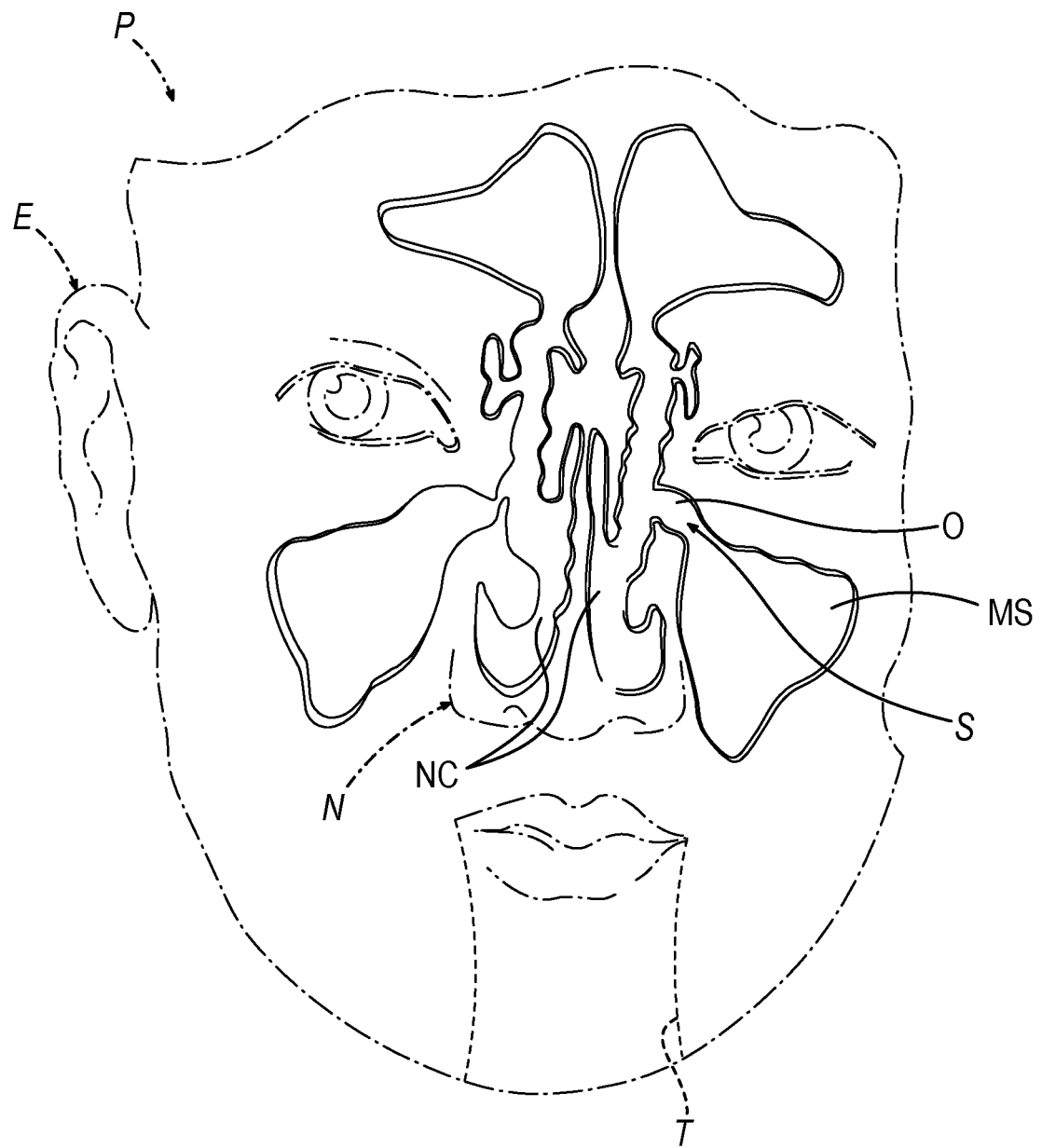
FIG. 10C depicts a front view of an ostium of the maxillary sinus, with the ostium having been enlarged by inflation of the dilation balloon of the dilation catheter of FIG. 4.

FIGS. 10A-10C show an exemplary method for using balloon dilation catheter (200) discussed above to dilate target anatomical structure (S) shown as a sinus ostium (O) of a maxillary sinus (MS) of the patient (P). While the present example is being provided in the context of dilating a sinus ostium (O) of a maxillary sinus (MS), it should be understood that balloon dilation catheter (200) may be used in various other procedures. By way of example only, balloon dilation catheter (200) and variations thereof may be used to dilate a Eustachian tube (shown and described above with reference to FIG. 8A-9C), a larynx, a choana, a sphenoid sinus ostium, one or more openings associated with one or more ethmoid sinus air cells, the frontal recess, and/or other passageways associated with paranasal sinuses. Other suitable ways in which balloon dilation catheter (200) may be used will be apparent to those skilled in the art in view of the teachings herein.

In the procedure of the present example, guide catheter (100) may be inserted transnasally and advanced through the nasal cavity (NC) to a position within or near the targeted anatomical structure (S) to be dilated (e.g. the sinus ostium (O)), as shown in FIG. 10A. This positioning of guide catheter (100) may be verified endoscopically with an endoscope such as endoscope (60) described above and/or by direct visualization, radiography, and/or by any other suitable method. After guide catheter (100) has been positioned, the operator may advance guidewire (80) distally through guide catheter (100) such that a distal portion of guidewire (80) passes through the sinus ostium (0) of the maxillary sinus (MS) and into the cavity of the maxillary sinus (MS) as shown in FIG. 10B.

FIG. 10B shows a front view of guide catheter (100) of FIG. 2A positioned adjacent an ostium of the maxillary sinus (MS), with balloon dilation catheter (200) of FIG. 4 translated distally relative to guide catheter (100) along guidewire (80) of FIG. 2A so as to position balloons (216a-d) of balloon assembly (206) within the sinus ostium (O). As shown in FIG. 10C, with guide catheter (100) and guidewire (50) suitably positioned, balloon dilation catheter (200) may be advanced along guidewire (50), and through distal end (106) of guide catheter (100), with balloon assembly (206) in a non-expanded state until balloon assembly (206) is positioned within the ostium (O) of the maxillary sinus (MS) (or another targeted anatomical structure). After balloon assembly (206) has been positioned within the sinus ostium (O), a dilation balloon (216a-d) of balloon assembly (206) may be inflated, thereby dilating the sinus ostium (O), as shown in FIG. 10C. As such, FIG. 10C shows a front view of sinus ostium (O) of the maxillary sinus (MS), with the sinus ostium (O) having been enlarged by inflation of dilation balloon (216a-d) of balloon assembly (206).

The transfer of fluid from inflation source (218) expands a dilation balloon (216a-c) to the expanded configuration to open/dilate the sinus ostium (O), such as by remodeling the bone, etc., forming the sinus ostium (O). By way of example only, balloon assembly (206) may be inflated to a volume sized to achieve a pressure of about 10 to about 12 atmospheres. Balloon assembly (206) may be held at this pressure for a few seconds to sufficiently open the ostium (O) (or other targeted anatomical structure (S)). Balloon assembly (206) may then be deflated to a non-expanded configuration by reversing the flow of fluid into inflation source (218). Balloon assembly (206) may be repeatedly inflated and deflated in different ostia and/or other targeted anatomical passageways. As described above, another dilation balloon (216a-d) of balloon assembly (206) may then be inflated, without having to first remove balloon dilation catheter (200) from the ostium (O), thereby simplifying the procedure and ensuring the same target anatomical structure (S) is being treated (e.g. dilated). Thereafter, guidewire (50), guide catheter (100), and balloon dilation catheter (200) may be removed from the patient (P), with the result of such being shown in FIG. 10C.

In some instances, it may be desirable to irrigate the sinus and paranasal cavity after balloon assembly (206) of balloon dilation catheter (200) has been used to dilate the sinus ostium (O). By way of example only, irrigation may be carried out in accordance with at least some of the teachings of U.S. Pat. No. 7,630,676, entitled "Methods, Devices and Systems for Treatment and/or Diagnosis of Disorders of the Ear, Nose and Throat," issued Dec. 8, 2009, the disclosure of which is incorporated by reference herein.

E. Exemplary Method for Dilating the ET from a Middle Ear Approach

According to another exemplary method, balloon dilation catheter (200) may be used to access the target anatomical structure (S) (e.g. the ET) using a middle ear approach. For example, balloon dilation catheter (200) shown and described herein may be configured in accordance with one or more teachings of U.S. Pat. No. 10,070,993, entitled "System and Method for Treatment of Eustachian Tube from Middle Ear Approach," issued on Sep. 11, 2018, the disclosure of which is incorporated by reference herein.

In some examples, guide catheter (100) may be used to aid in accessing the target anatomical structure (S) with balloon dilation catheter (200) through the ear canal (20). In addition, or in the alternative, a guiding element such as a guidewire or illuminating fiber (not shown) may be used to aid in accessing the target anatomical structure (S). Of course, such guidance features are merely optional. It should therefore be understood that balloon dilation catheters (200, 300) may be used to access the target anatomical structure (S) without the use of an additional guide catheter or guidewire, etc. Other illustrative methods are disclosed in U.S. Pat. No. 10,070,993, entitled "System and Method for Treatment of Eustachian Tube from Middle Ear Approach," incorporated by reference above.

F. Second Exemplary Balloon Dilation Catheter

FIGS. 11-13 show a second exemplary balloon dilation catheter (300) that is sized and configured to access the ear (E), the nose (N), or the throat (T) of the patient (P). Particularly, FIG. 11 shows a side elevational view of balloon dilation catheter (300) that may be used with guide catheter (100) of FIG. 2A, and FIG. 12 shows a schematic view of balloon dilation catheter (300) of FIG. 11. Balloon dilation catheter (300) is substantially similar to balloon dilation catheter (200) described above.

Similar to balloon dilation catheter (200), balloon dilation catheter (300) of the present example includes a hub (302), an elongate shaft (304), and a balloon assembly (306). Elongate shaft (304) includes a proximal portion (308) and a distal portion (310) disposed opposite proximal portion (308). Hub (302) is coupled with proximal portion (308) of elongate shaft (304). Elongate shaft (304) may include a guidewire lumen (342) configured to receive guidewire (80). Balloon assembly (306) may be coupled with distal portion (310) of elongate shaft (304) and is coaxially disposed along elongate shaft (304). As shown, elongate shaft (304) extends proximally from balloon assembly (306). Balloon assembly (306) is shown as being disposed proximal to a distal tip (340) of elongate shaft (304); however, this arrangement may vary in some versions.

Balloon assembly (306) includes at least two dilation balloons that at least partially overlap one another to form an overlapping series of dilation balloons.

Whereas balloon dilation catheter (200) includes inflation ports (212a-d), balloon dilation catheter (300) includes a valve (311), a single port (312) and balloons (316a-c). As shown, valve (311) includes valve outlets (212a-c) fluidly coupled with a respective inflation lumen (314a-c). As will be described in greater detail below, a user couples an inflation source (318) with valve (311), such that valve outlets (313a-c) are fluidly coupled with respective inflation lumen of inflation lumens (314a-c). Each of inflation lumens (314a-c) are fluidly coupled with respective dilation balloons of dilation balloons (316a-c). Each dilation balloon (316a-c) may be fed by a dedicated inflation lumen (314a-c) on a 1:1 basis. Greater or fewer valve outlets, inflation lumens, and dilation balloons are envisioned. For example, balloon dilation catheter (300) may include two valve outlets, two inflation lumens, and two dilation balloons. Alternatively, for example, balloon dilation catheter (300) may include four valve outlets, four inflation lumens, and four dilation balloons.

As shown in FIGS. 11-12, balloon dilation catheter (300) includes a single valve (311), where valve (311) includes at least first and second valve outlets with valve outlets (313a-c) being shown. Valve (311) may control re-directing the flow of the inflation fluid from inflation source (318) to the different dilation balloon (316a-c) of balloon assembly (306). Utilizing valve (311), balloon dilation catheter (300) may utilize a single port (312) coupled with inflation source (318) unlike inflation ports (212a-c) shown in FIGS. 4, 5, and 7 with respect to balloon dilation catheter (200).

Each individual balloon (316a-c) may be generally similar in construction and function to balloons (216a-c) described above. For instance, balloons (316a-c) are suitably sized and coupled with elongate shaft (304). This allows the user to achieve a predetermined dilation diameter (d1-d3) for a desired procedure by selecting the desired valve outlet (e.g. valve outlets (313a-c)) that corresponds to a particular dilation balloon (316a-c). This may prevent a user (e.g. a surgeon) from having to sequentially insert multiple balloon dilation catheters having different sized dilation balloons to treat the target anatomical structure (S).

As shown in FIG. 11, balloon dilation catheter (300) includes an actuator (320). Actuator (320) has a proximal side (322) and a distal side (324). As shown, hub (302) includes valve outlets (313a-c), elongate shaft (304) includes inflation lumens (314a-c), and balloon assembly (306) includes dilation balloons (316a-c). Similar to FIG. 6 regarding dilation balloons (216a-d), dilation balloons (316a-c) are approximately coextensive with one another along longitudinal axis (LA). Alternatively, for example, balloon dilation catheter (300) may include four valve outlets, four inflation lumens, and four dilation balloons. While not shown, if additional length is desired, multiple balloons may be used in series (e.g. distal and proximal balloons (not shown)) and may be placed and controlled with different lumens. Elongate shaft (304) may include a guidewire lumen (342), shown as being centrally disposed, configured to receive guidewire (80) therethrough.

FIG. 13 shows an enlarged elevational view of valve (311) of hub (302) of balloon dilation catheter (300) of FIG. 11. Hub (302) includes indicia (326a-c) near valve outlets (313a-c) indicating information regarding characteristics of dilation balloons (316a-c) respectively. This ensures that the desired inflation diameter (d1-d3) of balloon assembly (306) particularly matches indicia (326a-c) located on respective valve outlets (313a-c) of hub (302). For example, indicia (326a-c) may include dilation diameters (d1-d3), or a desired location for the specific diameter of the respective balloon, etc. As shown, hub (302) includes indicia near first and second outlets of valve indicating information regarding dilation balloons (316a-c).

A method of dilating the target anatomical structure (S) of the ear (E), the nose (N), or the throat (T) of the patient (P) is similar to that described above with reference to balloon dilation catheter (200). A distal portion (228) of balloon dilation catheter (200) may be positioned in the target anatomical structure (S) of the ear (E), the nose (N), or the throat (T) of the patient (P) with or without the assistance of a prepositioned guide catheter (10) and guidewire (80). A marker (344) (see FIG. 11) on elongate shaft (304) of balloon dilation catheter (300) may be viewed from endoscope (60) to approximate a location of balloon assembly (306).

Instead of using different ports (212a-d), valve (311) is manipulated to fluidly couple different inflation valve outlets (313a-c) with inflation lumens (314a-c) to achieve different dilation diameters (d1-d3) of dilation balloons (316a-c) in the expanded/inflated configuration. For example, dilation balloon (316a) may be selectively inflated to diameter (d1) to dilate target anatomical structure (S) by fluidly coupling inflation source (318) with port (312). Port (312) is fluidly coupled with valve outlet (313a) of valve (311). Valve outlet (313a) is in fluid communication with dilation balloon (316a) using first inflation lumen (314a) that extends through elongate shaft (304). Similarly, dilation balloon (316b) may be selectively inflated to diameter (d2) that is greater than diameter (d1) by fluidly coupling inflation source (318) with port (312). Port (312) is fluidly coupled with valve outlet (313b) of valve (311). Valve outlet (313b) is in fluid communication with dilation balloon (316b) using inflation lumen (314b) that extends through elongate shaft (304). Similarly, dilation balloon (316c) may be selectively inflated to diameter (d3) that is greater than diameters (d1, d2) by fluidly coupling inflation source (318) with port (312). Port (312) is fluidly coupled with valve outlet (313c) of valve (311). Valve outlet (313c) is in fluid communication with dilation balloon (316c) using inflation lumen (314c) that extends through elongate shaft (304).

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of dilating a target anatomical structure of an ear, a nose, or a throat of a patient, the method comprising: (a) inserting a distal end of a balloon catheter into the ear, the nose, or the throat of the patient, wherein the balloon catheter includes a balloon assembly coaxially disposed along a proximally extending shaft, wherein the balloon assembly includes at least first and second dilation balloons that at least partially overlap one another; (b) distally advancing the distal end of the balloon catheter until the balloon assembly is disposed in the target anatomical structure of the ear, the nose, or the throat of the patient; and (c) selectively dilating the target anatomical structure of the ear, the nose, or the throat of the patient based on a diameter of the target anatomical structure of the patient by: (i) inflating the first dilation balloon to a first diameter by communicating an inflation fluid through a first inflation lumen, or (ii) inflating the second dilation balloon to a second diameter that is greater than the first diameter by communicating the inflation fluid through a second inflation lumen, wherein the second inflation lumen is not in fluid communication with the first inflation lumen.

Example 2

The method of Example 1, wherein selectively dilating the target anatomical structure further comprises: (i) inflating the first dilation balloon to the first diameter by communicating the inflation fluid through the first inflation lumen, and (ii) inflating the second dilation balloon to the second diameter that is greater than the first diameter by communicating the inflation fluid through the second inflation lumen after inflating the first dilation balloon to the first diameter without removing the balloon assembly from the target anatomical structure.

Example 3

The method of any of the previous Examples, wherein inflating the first dilation balloon to the first diameter by communicating the inflation fluid through the first inflation lumen further comprises fluidly coupling the inflation source with a first port that is in fluid communication with the first dilation balloon using the first inflation lumen that extends through the shaft to selectively inflate the first dilation balloon to the first diameter to dilate the target anatomical structure, or inflating the second dilation balloon to the second diameter that is greater than the first diameter by communicating the inflation fluid through the second inflation lumen further comprises fluidly coupling the inflation source with a second port that is in fluid communication with the second dilation balloon using the second inflation lumen that extends through the shaft to selectively inflate the second dilation balloon to the second diameter to dilate the target anatomical structure.

Example 4

The method of Example 3, wherein balloon catheter includes a hub, wherein the hub includes first and second indicia near the first and second ports indicating information regarding the first and second dilation balloons.

Example 5

The dilation catheter of any one or more of the previous Examples, wherein the balloon catheter includes a valve, wherein the valve includes at least first and second valve outlets, wherein inflating the first dilation balloon to the first diameter by communicating the inflation fluid through the first inflation lumen further comprises fluidly coupling an inflation source containing the inflation fluid with the first valve outlet that is in fluid communication with the first dilation balloon using the first inflation lumen that extends through the shaft to selectively inflate the first dilation balloon to the first diameter to dilate the target anatomical structure, or wherein inflating the second dilation balloon to the second diameter that is greater than the first diameter by communicating the inflation fluid through the second inflation lumen further comprises fluidly coupling the inflation source with the second valve outlet that is in fluid communication with the second dilation balloon using the second inflation lumen that extends through the shaft to selectively inflate the second dilation balloon to the second diameter to dilate the target anatomical structure.

Example 6

The method of Example 5, wherein the valve includes first and second indicia near the first and second valve outlets of the valve indicating information regarding the first and second dilation balloons respectively.

Example 7

The method of any one or more of the previous Examples, wherein the first and second dilation balloons are approximately coextensive with one another along a longitudinal axis.

Example 8

The method of any one or more of the previous Examples, wherein the balloon assembly includes a third dilation balloon, wherein selectively dilating the target anatomical structure further comprises inflating the third dilation balloon to a third diameter that is greater than the first and second diameters by communicating the inflation fluid through a third inflation lumen, wherein the third inflation lumen is not in fluid communication with either of the first or second inflation lumens.

Example 9

The method of Example 8, wherein the first diameter is approximately 3 millimeters, the second diameter is approximately 5 millimeters, and the third diameter is approximately 6 millimeters.

Example 10

The method of Example 8, wherein the first diameter is approximately 6 millimeters, the second diameter is approximately 7 millimeters, and the third diameter is approximately 8 millimeters.

Example 11

The dilation catheter of any one or more of Examples 8 through 10, wherein selectively dilating the target anatomical structure of the ear, the nose, or the throat comprises selectively inflating one of the first, second, or third dilation balloons to a predetermined pressure.

Example 12

The dilation catheter of any one or more of Examples 8 through 11, wherein the balloon assembly includes a fourth dilation balloon, wherein selectively dilating the target anatomical structure further comprises inflating the fourth dilation balloon to a fourth diameter that is greater than the first, second, and third diameters by inserting the inflation fluid through a fourth inflation lumen, wherein the fourth inflation lumen is not in fluid communication with any of the first, second, or third inflation lumens.

Example 13

The dilation catheter of any one or more of the previous Examples, wherein the target anatomical structure is selected from the group consisting of a passageway associated with drainage of a sinus cavity or a Eustachian tube.

Example 14

The dilation catheter of any one or more of the preceding claims, further comprising inserting a guide into the ear, the nose, or the throat of a patient, wherein the balloon catheter is advanced along the guide to distally advance the distal end of the balloon catheter until the balloon assembly is disposed in the target anatomical structure.

Example 15

The dilation catheter of Example 14, wherein the guide includes a lumen, the method further comprising advancing the balloon catheter along the lumen of the guide.

Example 16

A method of dilating a target anatomical structure of an ear, a nasal cavity, or a throat of a patient, the method comprising: (a) inserting a distal end of a balloon catheter into the ear, the nose, or the throat of the patient, wherein the balloon catheter includes a balloon assembly coaxially disposed along a proximally extending shaft, wherein the balloon assembly includes at least first and second dilation balloons that at least partially overlap one another; (b) distally advancing the distal end of the balloon catheter until the balloon assembly is disposed in the target anatomical structure of a middle ear cavity, a sinus cavity, a nasal airway, or a Eustachian tube of the ear, the nose, or the throat of the patient; and (c) selectively dilating the target anatomical structure of the ear, the nasal cavity, or the throat based on a diameter of the target anatomical structure of the patient by: (i) inflating the first dilation balloon to a first diameter by communicating an inflation fluid through a first inflation lumen, or (ii) inflating the second dilation balloon to a second diameter that is greater than the first diameter by communicating the inflation fluid through a second inflation lumen, wherein the second inflation lumen is not in fluid communication with the first inflation lumen.

Example 17

The method of Example 16, wherein selectively dilating the target anatomical structure further comprises: (a) inflating the first dilation balloon to the first diameter by communicating an inflation fluid through the first inflation lumen, and (b) inflating the second dilation balloon to the second diameter that is greater than the first diameter by communicating the inflation fluid through the second inflation lumen after inflating the first dilation balloon to the first diameter without removing the balloon assembly from the target anatomical structure in the ear, the nasal cavity, or the throat.

Example 18

A method of dilating a target anatomical structure of an ear, a nose, or a throat of a patient, the method comprising: (a) inserting a distal end of a balloon catheter into the ear, the nose, or the throat of the patient, wherein the balloon catheter includes a balloon assembly coaxially disposed along a proximally extending shaft, wherein the balloon assembly includes at least first and second dilation balloons that at least partially overlap one another, wherein the first dilation balloon has a first diameter in an expanded configuration and the second dilation balloon has a second diameter in an expanded configuration that is greater than the first diameter; (b) distally advancing the distal end of the balloon catheter until the balloon assembly is disposed in the target anatomical structure of the ear, the nose, or the throat of the patient; and (c) selectively inflating one of the first or second dilation balloons to dilate the target anatomical structure of the ear, the nose, or the throat of the patient based on at least one of: (i) the size of the patient, or (ii) the target anatomical structure of the ear, the nose, or the throat being dilated.

Example 19

The method of Example 18, wherein selectively inflating one of the first or second dilation balloons to dilate the target anatomical structure further comprises: fluidly coupling an inflation source with a first port that is in fluid communication with the first dilation balloon using a first inflation lumen that extends through the shaft to selectively inflate the first dilation balloon to the first diameter to dilate the target anatomical structure, or fluidly coupling the inflation source with a second port that is in fluid communication with the second dilation balloon using a second inflation lumen that extends through the shaft to selectively inflate the second dilation balloon to the second diameter to dilate the target anatomical structure.

Example 20

The dilation catheter of any one or more of Examples 18 through 19, wherein the balloon assembly includes a third dilation balloon having a third diameter in an expanded configuration that is greater than either of the first or second diameters, wherein selectively inflating one of the first or second dilation balloons further comprises selectively inflating one of the first, second, or third dilation balloons to dilate the target anatomical structure of the ear, the nose, or the throat of the patient.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of dilating a target anatomical structure of an ear, a nose, or a throat of a patient, the method comprising:
   (a) inserting a distal end of a balloon catheter into the ear, the nose, or the throat of the patient, the balloon catheter including a balloon assembly coaxially disposed along a proximally extending shaft, the balloon assembly including at least first and second dilation balloons that at least partially overlap one another, the first and second dilation balloons including first and second unperforated balloon walls, respectively, the first and second dilation balloons each being configured to dilate the target anatomical structure independently of each other;
   (b) distally advancing the distal end of the balloon catheter until the balloon assembly is disposed in the target anatomical structure of the ear, the nose, or the throat of the patient; and
   (c) selectively dilating the target anatomical structure of the ear, the nose, or the throat of the patient based on a diameter of the target anatomical structure of the patient while directly contacting the target anatomical structure with an exterior surface of the first dilation balloon by:
   (i) inflating the first dilation balloon to a first diameter by communicating an inflation fluid through a first inflation lumen, the first inflation lumen extending longitudinally within the shaft and defining a first luminal space, or
   (ii) inflating the second dilation balloon to a second diameter that is smaller than the first diameter by communicating the inflation fluid through a second inflation lumen, the second inflation lumen extending longitudinally within the shaft and having a second luminal space that is independent from the first luminal space, and the second inflation lumen not being in fluid communication with the first inflation lumen.

2. The method of claim 1, the selectively dilating the target anatomical structure further comprising:
   (i) inflating the second dilation balloon to the second diameter by communicating the inflation fluid through the second inflation lumen, and
   (ii) inflating the first dilation balloon to the first diameter that is greater than the second diameter by communicating the inflation fluid through the first inflation lumen after inflating the second dilation balloon to the second diameter without removing the balloon assembly from the target anatomical structure.

3. The method of claim 1, the inflating the first dilation balloon to the first diameter by communicating the inflation fluid through the first inflation lumen further comprising fluidly coupling an inflation source with a first port that is in fluid communication with the first dilation balloon using the first inflation lumen that extends through the shaft to selectively inflate the first dilation balloon to the first diameter to dilate the target anatomical structure, or
   the inflating the second dilation balloon to the second diameter that is smaller than the first diameter by communicating the inflation fluid through the second inflation lumen further comprising fluidly coupling the inflation source with a second port that is in fluid communication with the second dilation balloon using the second inflation lumen that extends through the shaft to selectively inflate the second dilation balloon to the second diameter to dilate the target anatomical structure.

4. The method of claim 3, the balloon catheter including a hub, the hub including first and second indicia near the first and second ports indicating information regarding the first and second dilation balloons.

5. The method of claim 1, the balloon catheter including a valve, the valve including at least first and second valve outlets, and
   the inflating the first dilation balloon to the first diameter by communicating the inflation fluid through the first inflation lumen further comprising fluidly coupling an inflation source containing the inflation fluid with the first valve outlet that is in fluid communication with the first dilation balloon using the first inflation lumen that extends through the shaft to selectively inflate the first dilation balloon to the first diameter to dilate the target anatomical structure, or
   the inflating the second dilation balloon to the second diameter that is smaller than the first diameter by communicating the inflation fluid through the second inflation lumen further comprising fluidly coupling the inflation source with the second valve outlet that is in fluid communication with the second dilation balloon using the second inflation lumen that extends through the shaft to selectively inflate the second dilation balloon to the second diameter to dilate the target anatomical structure.

6. The method of claim 5, the valve including first and second indicia near the first and second valve outlets of the valve indicating information regarding the first and second dilation balloons respectively.

7. The method of claim 1, the first and second dilation balloons being approximately coextensive with one another along a longitudinal axis.

8. The method of claim 1, the balloon assembly including a third dilation balloon, and the selectively dilating the target anatomical structure further comprising inflating the third dilation balloon to a third diameter that is smaller than the first and second diameters by communicating the inflation fluid through a third inflation lumen extending within the shaft and having a third luminal space that is independent from the first and second luminal spaces, the third inflation lumen not being in fluid communication with either of the first or second inflation lumens.

9. The method of claim 8, the first diameter being approximately 6 millimeters, the second diameter being approximately 5 millimeters, and the third diameter being approximately 3 millimeters.

10. The method of claim 8, the first diameter being approximately 8 millimeters, the second diameter being approximately 7 millimeters, and the third diameter being approximately 6 millimeters.

11. The method of claim 8, the selectively dilating the target anatomical structure of the ear, the nose, or the throat comprising selectively inflating one of the first, second, or third dilation balloons to a predetermined pressure.

12. The method of claim 8, the balloon assembly including a fourth dilation balloon, and the selectively dilating the target anatomical structure further comprising inflating the fourth dilation balloon to a fourth diameter that is smaller than the first, second, and third diameters by inserting the inflation fluid through a fourth inflation lumen extending within the shaft and having a fourth luminal space that is independent from the first, second, and third luminal spaces, the fourth inflation lumen not being in fluid communication with any of the first, second, or third inflation lumens, and the first, second, third, and fourth inflation lumens each being radially offset from a guidewire lumen extending longitudinally within the shaft at the center of the shaft, such that the first, second, third, and fourth lumens are symmetrically located within the shaft and equally offset from the guidewire lumen, when seen in a cross-sectional view.

13. The method of claim 1, further comprising inserting a guide into the ear, the nose, or the throat of a patient, the balloon catheter being advanced along the guide to distally advance the distal end of the balloon catheter until the balloon assembly is disposed in the target anatomical structure.

14. The method of claim 13, the guide including a lumen, the method further comprising advancing the balloon catheter along the lumen of the guide.

15. The method of claim 1, the selectively dilating the target anatomical structure comprising:
inflating the first dilation balloon to the first diameter that is greater than the second diameter by communicating the inflation fluid through the first inflation lumen without first inflating the second dilation balloon to the second diameter.

16. A method of dilating a target anatomical structure of an ear, a nasal cavity, or a throat of a patient, the method comprising:
(a) inserting a distal end of a balloon catheter into the ear, the nose, or the throat of the patient, the balloon catheter including a balloon assembly coaxially disposed along a proximally extending shaft, the balloon assembly including at least first and second dilation balloons that at least partially overlap one another, the first and second dilation balloons including first and second unperforated balloon walls, respectively, the first and second dilation balloons each being configured to dilate the target anatomical structure independently of each other;
(b) distally advancing the distal end of the balloon catheter until the balloon assembly is disposed in the target anatomical structure of a middle ear cavity, a sinus cavity, a nasal airway, or a Eustachian tube of the ear, the nose, or the throat of the patient; and
(c) selectively dilating the target anatomical structure of the ear, the nasal cavity, or the throat based on a diameter of the target anatomical structure of the patient by:
(i) inflating the first dilation balloon to a first diameter such that an exterior surface of the first dilation balloon is in direct contact with an inner portion of the target anatomical structure by communicating an inflation fluid through a first inflation lumen, the first inflation lumen extending longitudinally along the shaft, or
(ii) inflating the second dilation balloon to a second diameter that is smaller than the first diameter by communicating the inflation fluid through a second inflation lumen, the second inflation lumen extending longitudinally along the shaft and being circumferentially offset from the first inflation lumen, the second inflation lumen not being in fluid communication with the first inflation lumen, and wherein the exterior surface of the uninflated first dilation balloon is in direct contact with the inner portion of the target anatomical structure.

17. The method of claim 16, the selectively dilating the target anatomical structure further comprising:
(a) inflating the second dilation balloon to the second diameter by communicating an inflation fluid through the second inflation lumen, and
(b) inflating the second first dilation balloon to the second first diameter that is greater than the second diameter by communicating the inflation fluid through the second first inflation lumen after inflating the second dilation balloon to the second diameter without removing the balloon assembly from the target anatomical structure in the ear, the nasal cavity, or the throat.

18. A method of dilating a target anatomical structure of an ear, a nose, or a throat of a patient, the method comprising:
(a) inserting a distal end of a balloon catheter into the ear, the nose, or the throat of the patient, the balloon catheter including a balloon assembly coaxially disposed along a proximally extending shaft, the balloon assembly including at least first and second dilation balloons that at least partially overlap one another, the first dilation balloon having a first diameter in an expanded configuration and the second dilation balloon having a second diameter in an expanded configuration that is smaller than the first diameter, the first and second dilation balloons including first and second unperforated balloon walls, respectively, the first and second dilation balloons each being configured to dilate the target anatomical structure independently of each other;
(b) distally advancing the distal end of the balloon catheter until the balloon assembly is disposed in the target anatomical structure of the ear, the nose, or the throat of the patient; and
(c) selectively inflating one of the dilation balloons to dilate the target anatomical structure of the ear, the nose, or the throat of the patient such that an exterior surface of the second dilation balloon is in direct contact with an inner wall of the target anatomical structure, based on at least one of:
  (i) the size of the patient, or
  (ii) the target anatomical structure of the ear, the nose, or the throat being dilated.

19. The method of claim 18, the selectively inflating one of the dilation balloons to dilate the target anatomical structure further comprising:
  fluidly coupling an inflation source with a first port that is in fluid communication with the first dilation balloon using a first inflation lumen that extends through the shaft to selectively inflate the first dilation balloon to the first diameter to dilate the target anatomical structure, or
  fluidly coupling the inflation source with a second port that is in fluid communication with the second dilation balloon using a second inflation lumen that extends through the shaft to selectively inflate the second dilation balloon to the second diameter to dilate the target anatomical structure.

20. The method of claim 18, the balloon assembly further comprising a third dilation balloon having a third diameter in an expanded configuration that is smaller than both of the first and second diameters, and the selectively inflating one of the dilation balloons further comprising selectively inflating one of the first, second, or third dilation balloons to dilate the target anatomical structure of the ear, the nose, or the throat of the patient.

* * * * *